(12) United States Patent
Efimov et al.

(10) Patent No.: US 8,391,995 B2
(45) Date of Patent: Mar. 5, 2013

(54) CARDIAC PACING USING THE INFERIOR NODAL EXTENSION

(75) Inventors: Igor R. Efimov, St. Louis, MO (US); William Hucker, St. Louis, MO (US)

(73) Assignee: The Washington University, St. Louis, MO (US)

( * ) Notice: Subject to any disclaimer, the term of this patent is extended or adjusted under 35 U.S.C. 154(b) by 628 days.

(21) Appl. No.: 12/518,343

(22) PCT Filed: Nov. 13, 2007

(86) PCT No.: PCT/US2007/023836
§ 371 (c)(1), (2), (4) Date: Sep. 2, 2009

(87) PCT Pub. No.: WO2008/063498
PCT Pub. Date: May 29, 2008

(65) Prior Publication Data
US 2010/0016917 A1    Jan. 21, 2010

Related U.S. Application Data

(60) Provisional application No. 60/865,512, filed on Nov. 13, 2006.

(51) Int. Cl.
*A61N 1/05* (2006.01)

(52) U.S. Cl. .......................... 607/122; 607/127

(58) Field of Classification Search .............. 607/17, 607/122, 127, 131
See application file for complete search history.

(56) References Cited

U.S. PATENT DOCUMENTS

| | | | |
|---|---|---|---|
| 3,729,008 A | 4/1973 | Berkovits | |
| 3,738,370 A | 6/1973 | Charms | |
| 3,942,536 A | 3/1976 | Mirowski et al. | |
| 4,136,703 A | 1/1979 | Wittkampf | |
| 4,384,585 A | 5/1983 | Zipes | |
| 4,727,877 A | 3/1988 | Kallok | |
| 5,107,834 A | 4/1992 | Ideker et al. | |
| 5,199,429 A | 4/1993 | Kroll et al. | |
| 5,265,600 A | 11/1993 | Adams et al. | |
| 5,275,621 A | 1/1994 | Mehra | |
| 5,282,836 A | 2/1994 | Kreyenhagen et al. | |
| 5,306,291 A | 4/1994 | Kroll et al. | |
| 5,330,509 A | 7/1994 | Kroll et al. | |
| 5,334,219 A | 8/1994 | Kroll | |
| 5,365,391 A | 11/1994 | Sugiyama et al. | |

(Continued)

FOREIGN PATENT DOCUMENTS

| | | |
|---|---|---|
| EP | 0 393 265 A1 | 10/1990 |
| EP | 1 062 971 A1 | 12/2000 |

(Continued)

OTHER PUBLICATIONS

Davidenko et al., "Stationary and drifting spiral waves of excitation in isolated cardiac muscle," Nature, vol. 355, pp. 349-351, Jan. 23, 1992.

(Continued)

*Primary Examiner* — Carl H Layno
*Assistant Examiner* — Erica Lee
(74) *Attorney, Agent, or Firm* — Patterson Thuente Christensen Pedersen, P.A.

(57) ABSTRACT

A device and method for providing stimulation to an inferior nodal extension of a heart. The method includes providing a lead comprising an electrode, positioning the electrode proximate an inferior nodal extension of a heart, and effecting at least one of activation, deactivation, or modulation of the electrode to provide stimulation to the inferior nodal extension.

20 Claims, 22 Drawing Sheets

U.S. PATENT DOCUMENTS

| | | | |
|---|---|---|---|
| 5,372,605 | A | 12/1994 | Adams et al. |
| 5,383,907 | A | 1/1995 | Kroll |
| 5,387,613 | A | 2/1995 | Goldberg et al. |
| 5,391,186 | A | 2/1995 | Kroll et al. |
| 5,403,356 | A | 4/1995 | Hill et al. |
| 5,405,363 | A | 4/1995 | Kroll et al. |
| 5,407,444 | A | 4/1995 | Kroll |
| 5,413,591 | A | 5/1995 | Knoll |
| 5,489,293 | A | 2/1996 | Pless et al. |
| 5,545,182 | A | 8/1996 | Stotts et al. |
| 5,545,204 | A | 8/1996 | Cammilli et al. |
| 5,562,708 | A | 10/1996 | Combs et al. |
| 5,620,464 | A | 4/1997 | Kroll et al. |
| 5,620,468 | A | 4/1997 | Mongeon et al. |
| 5,674,248 | A | 10/1997 | Kroll et al. |
| 5,676,687 | A | 10/1997 | Ayers |
| 5,683,429 | A | 11/1997 | Mehra |
| 5,766,226 | A | 6/1998 | Pedersen |
| 5,792,187 | A | 8/1998 | Adams |
| 5,797,967 | A | 8/1998 | KenKnight |
| 5,800,465 | A | 9/1998 | Thompson et al. |
| 5,813,999 | A | 9/1998 | Ayers et al. |
| 5,840,079 | A | 11/1998 | Warman et al. |
| 5,925,066 | A | 7/1999 | Kroll et al. |
| 5,928,270 | A | 7/1999 | Ramsey, III |
| 5,995,871 | A | 11/1999 | Knisley |
| 6,070,081 | A | 5/2000 | Takahashi et al. |
| 6,081,746 | A | 6/2000 | Pendekanti et al. |
| 6,085,116 | A | 7/2000 | Pendekanti et al. |
| 6,085,119 | A | 7/2000 | Scheiner et al. |
| 6,091,991 | A | 7/2000 | Warren |
| 6,094,596 | A | 7/2000 | Morgan |
| 6,157,859 | A | 12/2000 | Alt |
| 6,178,351 | B1 | 1/2001 | Mower |
| 6,185,459 | B1 | 2/2001 | Mehra et al. |
| 6,205,357 | B1 | 3/2001 | Ideker et al. |
| 6,233,483 | B1 | 5/2001 | Causey, III et al. |
| 6,246,906 | B1 | 6/2001 | Hsu et al. |
| 6,292,691 | B1 | 9/2001 | Pendekanti et al. |
| 6,327,500 | B1 | 12/2001 | Cooper et al. |
| 6,463,330 | B1 | 10/2002 | Rabinovitch et al. |
| 6,510,342 | B1 | 1/2003 | Park et al. |
| 6,526,317 | B2 | 2/2003 | Hsu et al. |
| 6,556,862 | B2 | 4/2003 | Hsu et al. |
| 6,567,698 | B2 | 5/2003 | Herleikson |
| 6,587,720 | B2 | 7/2003 | Hsu et al. |
| 6,711,442 | B1 | 3/2004 | Swerdlow et al. |
| 6,745,081 | B1 | 6/2004 | Helland et al. |
| 6,763,266 | B1 | 7/2004 | Kroll |
| 6,813,516 | B2 | 11/2004 | Ujhelyi et al. |
| 6,847,842 | B1 | 1/2005 | Rodenhiser et al. |
| 6,937,896 | B1 | 8/2005 | Kroll |
| 7,006,867 | B1 | 2/2006 | Kroll |
| 7,020,517 | B2 | 3/2006 | Weiner |
| 7,079,891 | B1 | 7/2006 | Kroll |
| 7,110,811 | B2 | 9/2006 | Wagner et al. |
| 7,113,822 | B1 | 9/2006 | Kroll |
| 7,120,490 | B2 | 10/2006 | Chen et al. |
| 7,127,292 | B2 | 10/2006 | Warman et al. |
| 7,139,611 | B1 | 11/2006 | Kroll et al. |
| 7,142,927 | B2 | 11/2006 | Benser et al. |
| 7,142,928 | B2 | 11/2006 | Sharma et al. |
| 7,155,286 | B1 | 12/2006 | Kroll et al. |
| 7,181,276 | B1 | 2/2007 | Province et al. |
| 7,480,351 | B2 | 1/2009 | Hiatt, Jr. et al. |
| 2002/0128565 | A1 | 9/2002 | Rudy |
| 2003/0083727 | A1 | 5/2003 | Casavant et al. |
| 2003/0220676 | A1* | 11/2003 | Helland .................. 607/122 |
| 2005/0096701 | A1* | 5/2005 | Donovan et al. .............. 607/2 |
| 2005/0154420 | A1 | 7/2005 | Diaz et al. |
| 2006/0161206 | A1 | 7/2006 | Efimov et al. |
| 2007/0021793 | A1 | 1/2007 | Voegele et al. |
| 2009/0062877 | A1 | 3/2009 | Krinski et al. |
| 2009/0204164 | A1 | 8/2009 | Efimov et al. |
| 2011/0009916 | A1 | 1/2011 | Efimov et al. |

FOREIGN PATENT DOCUMENTS

| | | |
|---|---|---|
| GB | 2 025 236 A | 1/1980 |
| WO | WO 96/11035 | 4/1996 |
| WO | WO 2006/042295 | 4/2006 |
| WO | WO 2008/063498 A1 | 4/2008 |

OTHER PUBLICATIONS

Gray et al., "Spatial and temporal organization during cardiac fibrillation," Nature, vol. 392, pp. 75-78, May 14, 1998.

Witkowski et al, "Spatiotemporal evolution of ventricular fibrillation," Nature, vol. 392, pp. 78-82, Mar. 5, 1998.

Cherry et al, "Visualization of spiral and scroll waves in simulated and experimental cardiac tissue", New J. Phys., vol. 10, pp. 125016-125059, 2008.

Koster et al., "A randomized trial comparing monophasic and biphasic waveform shocks for external cardioversion of atrial fibrillation," Am. Heart. J. vol. 147, pp. e1-e7, 2004.

Babbs et al., "Therapeutic indices for transchest defibrillator shocks: Effective, damaging, and lethal electrical doses," Am. Heart J., vol. 99, No. 6, pp. 734738, Jun. 1980.

Santini et al., "Single Shock Endocavitary Low Energy Intracardiac Cardioversion of Chronic Atrial Fibrillation," J. Interv. Card. Electrophysiol., vol. 3, pp. 45-51, 1999.

Sakurai et al., "Design and Control of Wave Propagation Patterns in Excitable Media," Science, vol. 296, pp. 2009-2012, Jun. 14, 2002.

Rappel et al, "Spatiotemporal Control of Wave Instabilities in Cardiac Tissue," Phys. Rev. Lett., vol. 83, No. 2, pp. 456-459, Jul. 12, 1999.

Fenton et al., "Multiple mechanisms of spiral wave breakup in a model of cardiac electrical activity," Chaos, vol. 12, No. 3, pp. 852-892, Sep. 2002.

Fenton et al., "Vortex dynamics in three-dimensional continuous myocardium with fiber rotation: Filament instability and fibrillation," Chaos, vol. 8, No. 1, pp. 20-47, Mar. 1998.

Mackenzie, "Making sense of a heart gone wild," Science, vol. 303, pp. 786-787, Feb. 6, 2004.

Walcott et al., "Do clinically relevant transthoracic defibrillation energies cause myocardial damage and dysfunction?" Resuscitation, vol. 59, pp. 59-70, 2003.

Fenton et al., "Termination of Atrial Fibrillation Using Pulsed Low-Energy Far-Field Stimulation," Circulation, vol. 120, pp. 467-476, 2009.

Plonsey, "The Nature of Sources of Bioelectric and Biomagnetic Fields," Biophys. J., vol. 39, pp. 309-312, 1982.

Fast et al., "Activation of Cardiac Tissue by Extracellular Electrical Shocks: Formation of 'Secondary Sources' at Intercellular Clefts in Monolayers of Cultured Myocytes," Circ. Res., vol. 82, pp. 375-385, 1998.

Sambelashvili et al., "Virtual electrode theory explains pacing threshold increase caused by cardiac tissue damage," Am. J. Physiol. Heart Circ. Physiol., vol. 286, pp. H2183-H2194, 2004.

Hooks et al, "Cardiac Microstructure: Implications for Electrical Propagation and Defibrillation in the Heart," Circ. Res., vol. 91, pp. 331-338, 2002.

Trayanova et al., "Modeling Defibrillation: Effects of Fiber Curvature," J. Electrocardiol., vol. 31 (suppl.), pp. 23-29, 1998.

Roth et al., "A Bidomain Model for the Extracellular Potential and Magnetic Field of Cardiac Tissue," IEEE Trans. Biomed. Eng., vol. 33, No. 4, pp. 467-469, Apr. 1986.

Murray, "The Physiological Principle of Minimum Work: I. The Vascular System and the Cost of Blood Volume," Proc. Natl. Acad. Sci. USA, vol. 12, pp. 207-214, 1926.

Kassab, "Scaling laws of vascular trees: of form and function," Am. J. Physiol. Heart Circ. Physiol., vol. 290, pp. H894-H903, 2006.

Maleckar et al., "Polarity reversal lowers activation time during diastolic field stimulation of the rabbit ventricles: insights into mechanisms," Am. J. Physiol. Heart Circ. Physiol., vol. 295, pp. H1626-1633, 2008.

Kirchhof et al, "Regional entrainment of Atrial Fibrillation Studied by High-Resolution Mapping in Open-Chest Dogs," Circulation, vol. 88, pp. 736-749, 1993.

Pumir et al, "Wave Emission from Heterogeneities Opens a Way to Cotnrolling Chaos in the Heart," Phys. Rev. Lett., vol. 99, pp. 208101-1, 2007.

Gray et al, "Termination of spiral waves during cardiac fibrillation via shock-induced phase resetting," Proc. Natl. Acad. Sci. USA, vol. 102, No. 13, pp. 4672-4677, Mar. 29, 2005.

International Preliminary Report on Patentability for International Application No. PCT/US2005/040187 dated Feb. 24, 2009, 6 pages.

Ladwig et al., "Absence of an Impact of Emotional Distress on the Perception of Intracardiac Shock Discharges," International Journal of Behavioral Medicine, 2003, 10(1):56-65, USA.

Fishler et al., "Spatiotemporal Effects of Syncytial Heterogeneities on Cardiac Far-field Excitations during Monophasic and Biphasic Shocks", Journal of Cardiovascular Electrophysiolgy, 1998, 9(12):1310-24, USA.

Efimov et al., "Virtual Electrode-Induced Phase Singularity: A Basic Mechanism of Defibrillation Failure," Circulation Research, 1998, 82(8):918-25, USA.

Efimov et al., "Transmembrane Voltage Changes Produced by Real and Virtual Electrodes During Monophasic Defibrillation Shock Delivered by an Implantable Electrode," Journal of Cardiovascular Electrophysiolgy, 1997, 8(9):1031-45, USA.

Cheng et al., "Virtual Electrode-Induced Reexcitation: A Mechanism of Defibrillation," Circulation Research, 1999, 85(11):1056-66, USA.

Fishler, "Syncytial Heterogeneity as a Mechanism Underlying Cardiac Far-Field Stimulation During Defibrillation-Level Shocks," Journal of Cardiovascular Electrophysiolgy, 1998, 9(4):384-94, USA.

Tsukerman et al., "Defibrillation of the Heart by a Rotating Current Field," Kardiologiia, 1973, 13(12):75-80, USA.

Zheng et al., "Reduction of the Internal Atrial Defibrillation Threshold with Balanced Orthogonal Sequential Shocks," Journal of Cardiovascular Electrophysiolgy, 2002, 13(9):904-9, USA.

Hucker et al., "Atrioventricular conduction with and without AV nodal delay: two pathways to the bundle of His in the rabbit heart", Am J. Physiol. Heart Circ. Physiol., 2007, 293:H1122-H1130, USA.

Mowrey et al., "Membrane Time Constant During Internal Defibrillation Strength Shocks in Intact Heart: Effects of $Na^+$ and $Ca^{2+}$ Channel Blockers," J. Cardiovascular Electrophysiology, Apr. 25, 2004, Jun. 8, 2008, and Jan. 2009, 20(1):85-92, USA.

European Patent Office, European Office Action for European Application No. 05825356.8, dated Oct. 5, 2009, 6 pages, Munich, Germany.

Korean Intellectual Property Office, PCT Written Opinion for International Application No. PCT/US2008/086483, dated Jun. 25, 2009, 7 pages, Daejeon, Korea.

Application and File History for U.S. Appl. No. 12/776,196, filed May 7, 2010. Inventors: Igor Efimov et al.

Peters et al., "Disturbed Connexin43 Gap Junction Distribution Correlates With the Location of Reentrant Circuits in the Epicardial Border Zone of Healing Canine Infarcts That Cause Ventricular Tachycardia," Circulation, 1997, 95:988-996, USA.

Niemann et al., "Intracardiac Voltage Gradients during Transthoracic Defibrillation: Implications for Postshock Myocardial Injury," Acad. Emerg. Med., Feb. 2005, 12(2):99-105, USA.

Kodama et al., "Aftereffects of high-intensity DC stimulation of the electromechanical performance of ventricular muscle", Am J. Physiol., 1994, 267:H248-H258, USA.

Li et al., "Defribillation Shocks Produce Different Effects on Purkinje Fibers and Ventricular Muscle: Implications for Successful Defibrillation, Refibrillation and Postshock Arrhythmia", J Am Coll Cardiol, 1993, 22:607-614, USA.

Zhou et al., "Epicardial Mapping of Ventricular Defibrillation With Monophasic and Biphasic Shocks in Dogs," Circulation Research, Jan. 1993, 72(1):145-160, USA.

Li et al., "Mechanisms of enhanced shock-induced arrhythmogenesis in the rabbit heart with healed myocardial infaraction," Am. J. Physiol. Heart Circ Physiol., May 3, 2005, 289:H1054-H1068, USA.

Sambelashvili et al., "Nonlinear effects in subthreshold virtual electrode polarization," Am. J. Physiol. Heart Circ, Physiol., 2003, 284(6):H2368-H2374, USA.

Aguel et al., "Advances in Modeling Cardiac Defibrillation," Int'l Journal of Bifurcation & Chaos, 2003, 13(12):3791-3803, World Scientific Publishing Company, USA.

Hillebrenner et al., "Postshock arrhythmogenesis in a slice of the canine heart," J. Cardiovasc. Electrophys., 2003, 14:S249-S256, Department of Biomedical Engineering, Tulane University, New Orleans, Louisiana USA.

Trayanova et al., "Virtual Electrode-Induced Positive and Negative Graded Responses: New Insights into Fibrillation Induction and Defibrillation," J. Cardiovascular Electrophysicology, 2003, 14(7):756-763, Department of Biomedical Engineering, Tulane University, New Orleans, Louisiana and Department of Biomedical Engineering, University of Alabama, Birmingham, Alabama, USA.

Larson et al., "Analysis of Electrically-Induced Reentrant Circuits in a Sheet of Myocardium," Annals Biomed. Eng., 2003, 31:768-780, USA.

Efimov, "Filbrillatin or Neurillation: Back to the future in our concepts of sudden cardiac death?", Circ. Res., May 30, 2003, 92(10):1062-1064, USA.

Efimov et al., "Diastolic Shocking Experience: Do Virtual Anodes Exist Only During Systole?", J. Cardiovascular Electrophysiology, Nov. 2003, 14(11):1223-1224, USA.

Efimov et al., Fast Fluorescent Mapping of Electrical Activity in the Heart: Practical Guide to Experimental Design and Applications, Chapter 7, pp. 131156, USA.

Cheng et al., "Shock-induced arrhythmogenesis is enhanced by 2,3-butanedione monoxime compared with cytochalasin D," Am. J. Physiol. Heart Circ. Physiol., 2004, 286:H310-H318, USA.

Takagi et al., "Unpinning and Removal of a Rotating Wave in Cardiac Muscle", Phys. Review Letters, Jul. 30, 2004, 93(5):058101-1-058101-4, The American Physical Society, USA.

Li et al., "Effects of Lidocaine on Shock-Induced Vulnerability", J. Cardiovascular Electrophysiology, Oct. 2003, 14(10):S237-S248, USA.

Cheng et al., "Mechanisms of Shock-Induced Arrhythmogenesis During Acute Global Ischemia", Am J Physiol. Heart Circ. Physiol., Jun. 2002, 282(6):H2141-51, American Physiological Society, USA.

Qu et al., "Mechanisms of Superiority of Ascending Ramp Waveforms: New Insights into Mechanisms of Shock-induced Vulnerability and Defibrillation," Am. J. Physiol. Heart Circ. Physiol., 2005, 289:H569-H577, American Physiological Society, USA.

Ashihara et al., "Spiral Wave Control by a Localized Stimulus: A Bidomain Model Study," J. Cardiovascular Electrophysiology, Feb. 2004 15(2):226-233, USA.

Ramanathan, "Noninvasive electrocardiographic imaging for cardiac electrophysiology and arrhythmia," Nature Medicine, Apr. 2004, 10(4):422-428, USA.

Nikolski et al., "Fluorescent Imaging of a Dual-Pathway Atrioventricular-Nodal Conduction System," Circ Res., Feb. 16, 2001, pp. 1-7, USA.

Qu et al., "The Gurvich waveform has lower defibrillation threshold than the Zoll waveform and the truncated exponential waveform in the rabbit heart," Can. J. Physiol. Pharmacol., 2005, 83:152-160, Canada.

Grosu et al., "Learning and Detecting Emergent Behavior in Networks of Cardiac Myocytes", Communications of the ACM, Mar. 2009, pp. 97-104, vol. 52, No. 3, USA.

Ripplinger et al., "Mechanisms of unpinning and termination of ventricular tachycardia", AM J. Physiol. Heart Circ. Physiol., 2006, pp. H184-H192, American Physiological Society, USA.

Sepulveda et al., "Current injection into a two-dimensional anisotropic bidomain", Biophys. J., vol. 55, May 1989, pp. 987-999, USA.

Allessie et al., "Regional Control of Atrial Fibrillation by Rapid Pacing in Conscious Dogs", Circulation, vol. 84, No. 4, Oct. 1991, pp. 1689-1697, USA.

Daoud et al., "Response of Type I Atrial Fibrillation to Atrial Pacing in Humans", Circulation, vol. 94, No. 5, 1996, 13 pages, USA.

Disertori et al., "Antitachycardia pacing therapies to terminate atrial tachyarrhythmias: the AT500 Italian Registry", European Heart Journal Supplements, 2001, pp. 16-24, USA.

Pumir et al., "Unpinning of a Rotating Wave in Cardiac Muscle by an Electric Field", J. Theor. Biol., vol. 199, 1999, pp. 311-319, USA.

Japanese Office Action for Japanese Patent Application No. 2009-537186, 7 pages, Oct. 11, 2012.

* cited by examiner

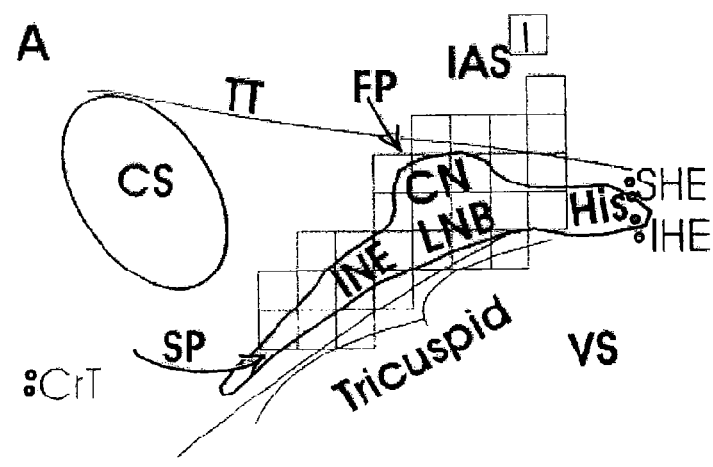
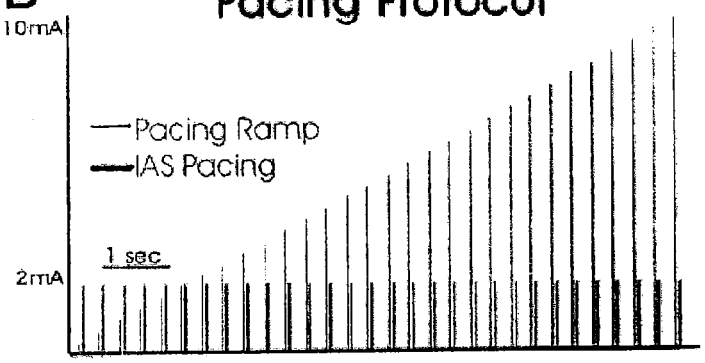
*Fig. 8*

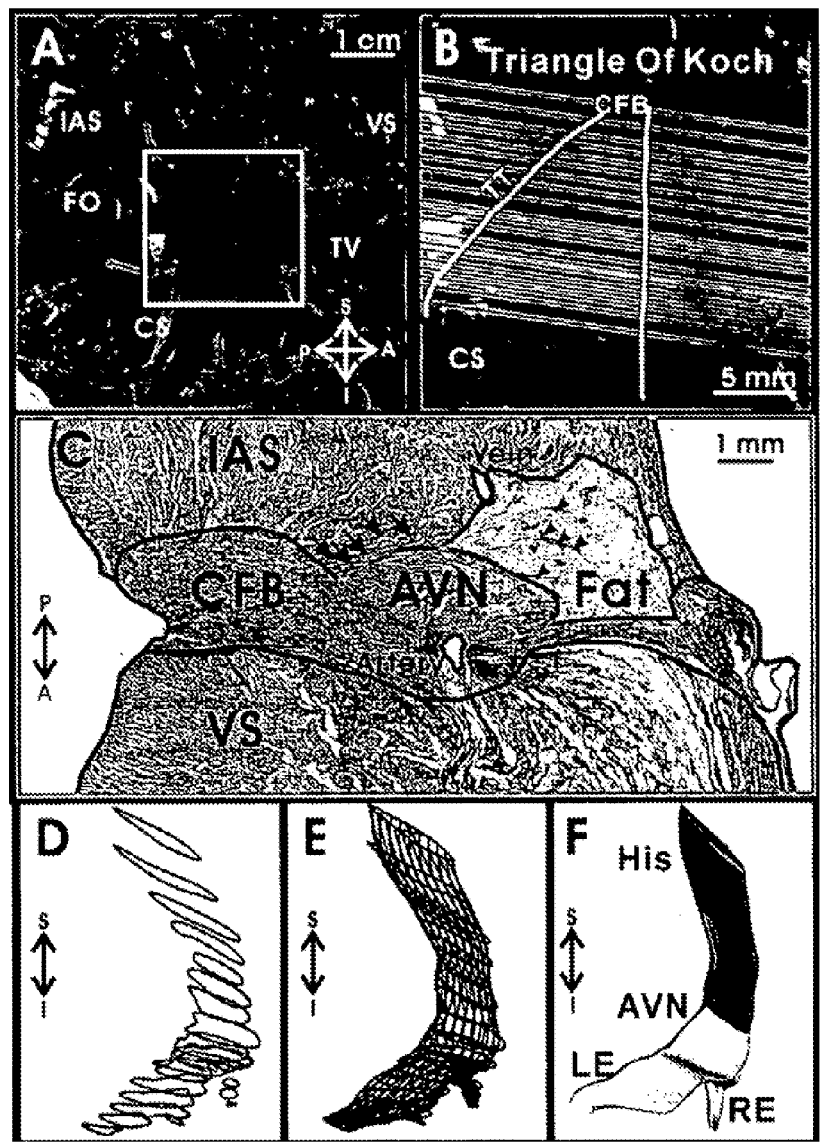

Dissection of human AV junction and creation of 3D reconstruction. A: Dissected AV junctional preparation with anatomical landmarks labeled. B: High resolution image of the boxed area in A, with locations of sections stained with Masson trichrome marked. Also the triangle of Koch is outlined, which is bounded by the tendon of Todaro (TT), the coronary sinus (CS) and the septal leaflet of the tricuspid valve (TV). C: Masson trichrome staining of section marked by a red line in B with different tissue areas outlined for 3D reconstruction. D: Outlines of the conduction system of all sections aligned in three dimensions. Red outline corresponds to the AV node outlined in C. E: Outlines of the conduction system lofted to create a 3D mesh. F: 3D mesh in E rendered to approximate the 3D volume. AVN: AV node; CFB: central fibrous body; FO, fossa ovalis. IAS: intratrial septum; LE: leftward extension; RE: rightward extension; VS: ventricular septum; S,I,P,A: Superior, inferior, posterior, anterior orientation.

137x193mm (300 x 300 DPI)

*Fig. 15*

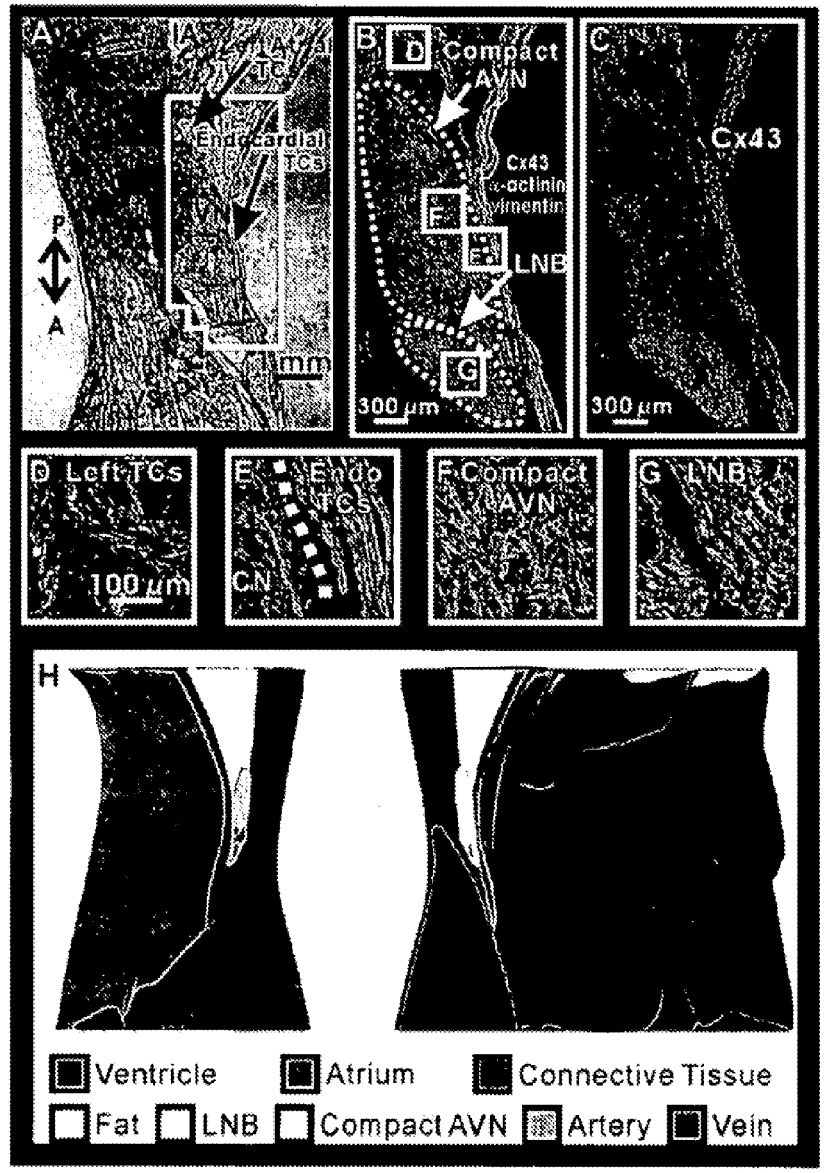

Cx43 density in the AV node. A: Masson trichrome stain of the AVN. Outlined area surrounding the AVN corresponds to immunohistochemistry shown in panels B and C. B: Immunohistochemistry of the AVN showing $\alpha$-actinin in red, vimentin in blue, and Cx43 in green. C: Cx43 expression in the AVN. D-G: Higher magnification of Cx43, vimentin, and $\alpha$-actinin expression in various areas of the AVN region. H: 3D reconstruction of the AVJ split open at the plane of section shown in panels A-C. CFB: central fibrous body; IAS: interatrial septum; LNB: lower nodal bundle; VS: ventricular septum; P,A: Posterior-anterior orientation.
103x146mm (350 x 350 DPI)

*Fig. 17*

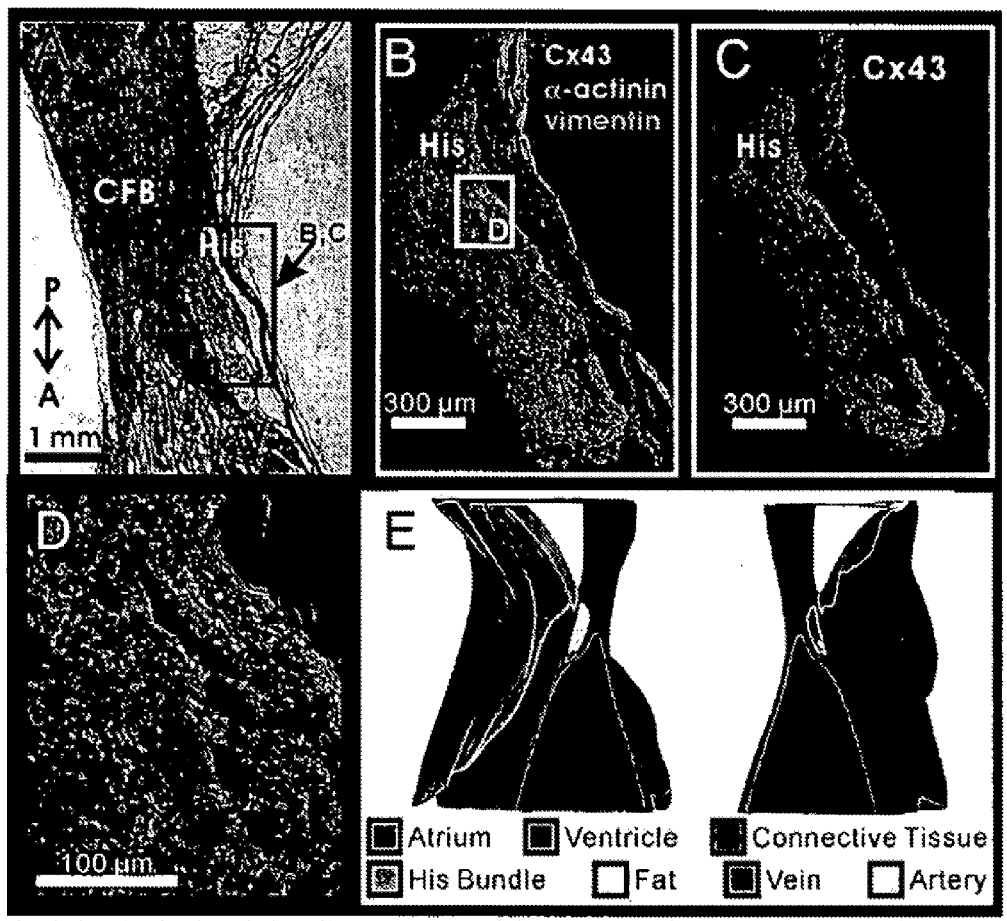

Cx43 density in the His bundle. A: Masson trichrome stain of the His bundle. Outlined area surrounding the His bundle corresponds to immunohistochemistry shown in panels B and C. B: Immunohistochemistry of the His bundle showing α-actinin in red, vimentin in blue, and Cx43 in green. C: Cx43 expression in the His bundle. D: Higher magnification of Cx43, vimentin, and α-actinin expression in the His bundle. E: 3D reconstruction of the AVJ which was split open at the plane of section shown in panels A-C. CFB: central fibrous body; IAS: interatrial septum; VS: ventricular septum; P,A: Posterior-anterior orientation.
141x127mm (350 x 350 DPI)

Fig. 18

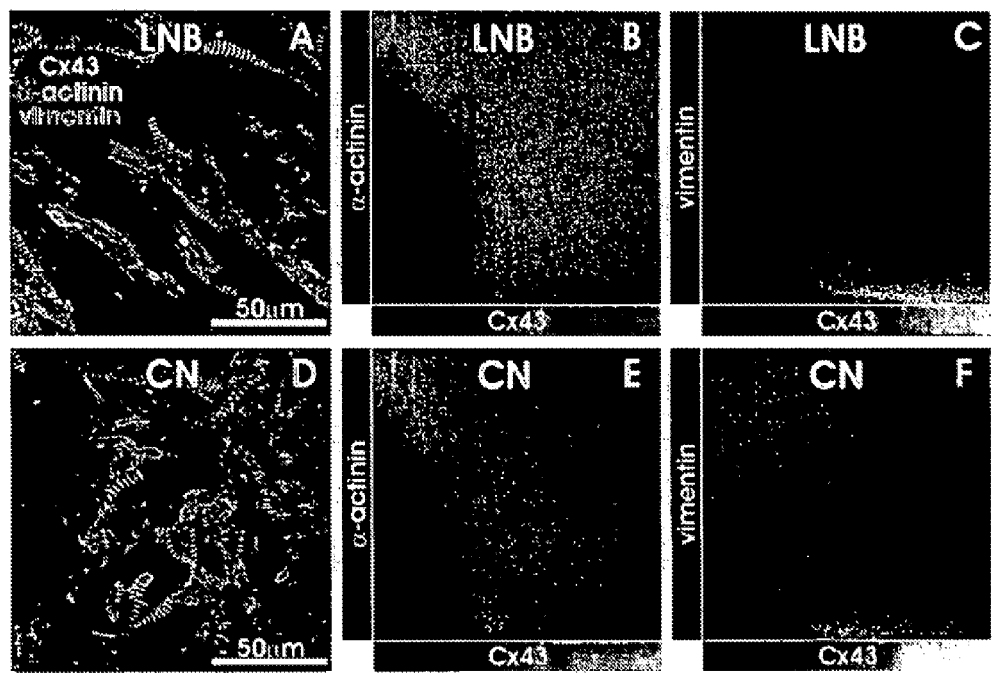

Cellular Expression of Cx43. A: maximum projection image of Cx43 (green) $\alpha$-actinin (red) and vimentin (blue) staining in the lower nodal bundle (LNB). B: Colocalization of Cx43 and $\alpha$-actinin, showing that voxels of high Cx43 intensity also have a high $\alpha$-actinin signal. C: Colocalization of Cx43 and vimentin, showing that voxels of high Cx43 intensity have no significant vimentin signal. D-E: Data similar to A-C for the compact node (CN). See text for details.
217x144mm (300 x 300 DPI)

*Fig. 19*

Cx43 density in transitional cells in the AVJ. Cx43 density in the endocardial (endo), left sided, and inferior transitional cells. All densities are normalized to the Cx43 density of the interatrial septum (IAS). DCM: dilated cardiomyopathy.
107x110mm (600 x 600 DPI)

| Heart | IAS | His | IAS | CN | LNB | IAS | LE | RE |
|---|---|---|---|---|---|---|---|---|
| 1 | 3.42 | 1.68 | 3.92 | 0.153 | 1.44 | 3.42 | 0.209 | 0.97 |
| 2 | 4.15 | 2.35 | 6.42 | 0.505 | 5.46 | 8.38 | 0.088 | 3.76 |
| 3 | 6.59 | 3.61 | 4.83 | 1.377 | 2.61 | 8.96 | | 0.91 |
| 4 (DCM) | 13.47 | 4.08 | 7.85 | 0.609 | 1.91 | 14.28 | 1.124 | 13.42 |
| Average | 6.91 | 2.93 | 5.76 | 0.661 | 2.86 | 8.76 | 0.473 | 4.76 |
| Ratio*100 | | 48±12% | | 12±11% | 50±26% | | 5±4% | 44±36% |

Cx43 density in the conduction system of the AVJ. All densities are normalized to the Cx43 density of the interatrial septum (IAS). CN: compact AVN; DCM: dilated cardiomyopathy; LNB: lower nodal bundle; LE: leftward extension; RE: rightward extension.
83x60mm (600 x 600 DPI)

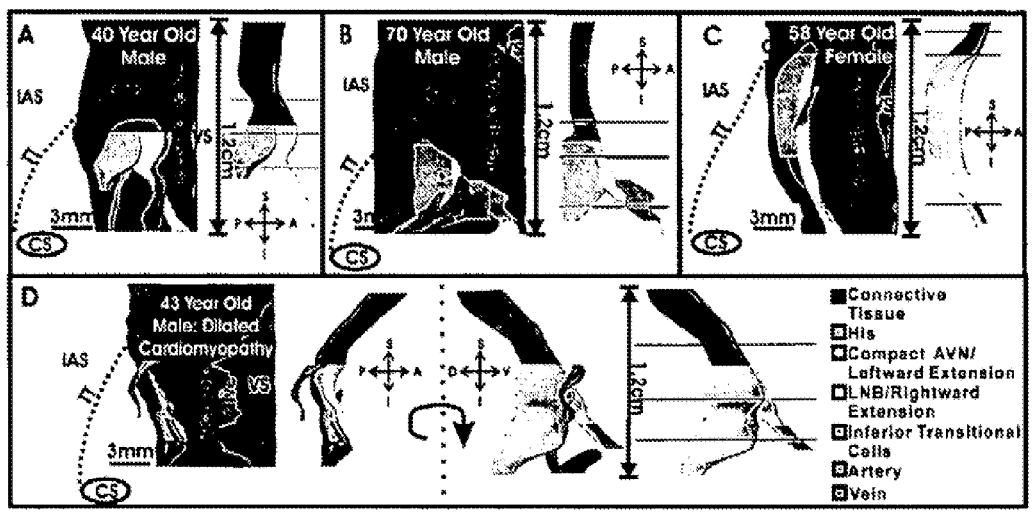

3D reconstruction of the AVJ conduction system. A-C: endocardial view of the conduction system of each normal heart. Left side of each panel displays the connective tissue and blood vessels surrounding the conduction system, as well as the location of the conduction system within the triangle of Koch of each preparation. Right side of each panel shows the conduction system and the three planes where Cx43 was quantified. D: Conduction system reconstruction of the heart with dilated cardiomyopathy. Left side of panel displays the same endocardial view as shown in A-C. Middle of panel shows the conduction system rotated 90° to more clearly show leftward extension. CFB: central fibrous body; IAS: interatrial septum; TT: tendon of Todaro; VS: ventricular septum. A-P, S-I, D-V: anterior-posterior, superior-inferior, and dorsal-ventral orientations.
89x43mm (600 x 600 DPI)

*Fig. 22*

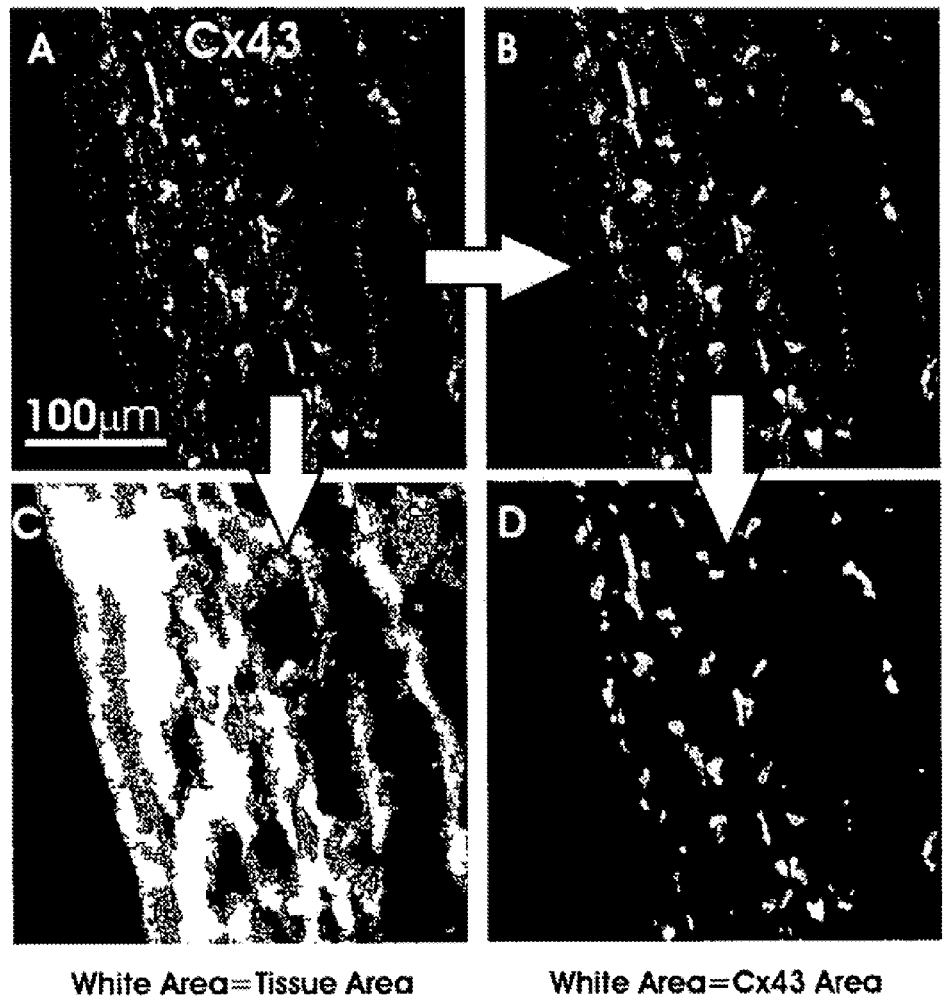

Cx43 Quantification. A: Photograph of Cx43 staining. B: Image thresholded to select Cx43 staining. C: The same image thresholded to select any tissue within the image. D: The thresholded image in B with the small areas above threshold removed and any black holes completely surrounded by white pixels filled. Connexin density was computed as: density=[(Cx43 area)/(tissue area)]*100.
188x219mm (300 x 300 DPI)

*Fig. 23*

| Heart | Sex | Age | Cause of Death |
|---|---|---|---|
| 1 | M | 40 | Brain Tumor |
| 2 | M | 70 | Intercerebral Hemorrhage |
| 3 | F | 58 | Intercerebral Hemorrhage |
| 4 | M | 43 | Explanted: Idiopathic Dilated Cardiomyopathy |
| Patient characteristics for each sample used in this study 172x50mm (300 x 300 DPI) | | | |

FIG. 24

CARDIAC PACING USING THE INFERIOR NODAL EXTENSION

RELATED APPLICATION

The present application claims the benefit of U.S. Provisional Application No. 60/865,512, filed Nov. 13, 2006, which is incorporated herein in its entirety by reference.

FIELD

The present disclosure relates generally to cardiac pacing. More particularly, the embodiments of the present disclosure relate to cardiac pacing using the inferior nodal extension ("INE") in the right atrium ("RA").

BACKGROUND

In a healthy heart, a heartbeat originates in the RA in the sinoatrial ("SA") node. Activation spreads quickly across the atria to the atrioventricular ("AV") node, which then delays the wave of excitation. The delay enables the atria to contract before the ventricles contract. After the activation is delayed by, and leaves, the AV node, it enters and excites the bundle of His. This excitation of the bundle of His spreads in a precise pattern to the ventricles through the ventricular conduction system composed of Purkinje fibers. Excitation spreading through this system activates each ventricular cell at a precise time to produce a coordinated ventricular contraction.

For various reasons, the AV node can be blocked (referred to as "AV block"), thus inhibiting or preventing utilization of the normal conduction system of the heart. AV block can also be therapeutically induced for rate control in patients with atrial fibrillation.

Ventricular pacing has been used for treating heart rhythm disorders when the normal conduction system of the heart can not be utilized due to AV block. However, ventricular pacing does not provide a high degree of electrical synchrony in the ventricular cells that is required for optimal mechanical function of the heart. As has been recently discovered, over long term, this can result in an increased occurrence of congestive heart failure.

One specific type of ventricular pacing is pacing from the right ventricular ("RV") apex of the heart. RV pacing has been used due to the stability of the type of lead and the ease of lead placement. Examples of venous pacing leads and electrodes for RV pacing are described in U.S. Pat. No. 6,094,596. However, direct RV pacing can lead to suboptimal ventricular performance, such as desynchronized contractions, negative inotropic effects, histological and ultrastructural changes in ventricular tissue, risks of congestive heart failure complications, and even death.

Due to these drawbacks of RV pacing, alternative pacing sites, such as the RV outflow tract ("RVOT") and various septal sites, have been explored to improve cardiac hemodynamics during pacing. Further, resynchronization therapy has been advanced by utilizing multiple ventricular pacing sites, such as biventricular pacing. However, the required physiological degree of synchrony may not be achieved using these alternative pacing methods. In addition, the clinical consequences of RVOT pacing are unknown.

Direct His bundle pacing has also been used in an attempt to achieve synchronized ventricular contraction in patients with an intact ventricular conduction system. However there can be limitations associated with His bundle pacing in humans. For example, studies have reported difficulty in pacing the relatively small area of the His bundle and difficulty inserting a pacing lead into the membranous septum. Further, higher pacing and lower sensing thresholds can be required for His pacing than for RV pacing due to the high fibrous content of the His region. Also, because His bundle pacing site is located close to aorta, there are potential, devastating consequences of damage of the aorta.

Accordingly there is a need for improved cardiac pacing devices and methods overcoming the deficiencies with conventional cardiac pacing.

BRIEF SUMMARY

Cardiac pacing methods and systems according to embodiments of the present disclosure exploit the coupling between the INE and the His bundle to achieve His bundle excitation without engaging the compact AV node. In an embodiment, this can be accomplished by using the INE located in the RA to excite the bundle of His directly and effectively bypass the AV node.

In an embodiment, a method of providing stimulation to an inferior nodal extension of a heart includes providing a lead including an electrode, positioning the electrode proximate an inferior nodal extension of a heart, and effecting at least one of activation, deactivation, or modulation of the electrode to provide stimulation to the inferior nodal extension.

In another embodiment, a method of pacing a heart includes providing a lead including an electrode, positioning the electrode within an anatomically effective distance to provide stimulation to an inferior nodal extension, such as within about 5-6 mm of the tricuspid valve within the triangle of Koch of the heart for humans, and effecting at least one of activation, deactivation, or modulation of the electrode to excite a bundle of His of the heart to produce synchronized ventricular contractions.

In a further embodiment, a method of providing stimulation to an inferior nodal extension of a heart includes providing a lead including an electrode and providing instructions to effect movement of the lead such that the electrode is positioned proximate an inferior nodal extension of a heart and effect at least one of activation, deactivation, or modulation of the electrode to provide stimulation to the inferior nodal extension.

A device for providing stimulation to an inferior nodal extension including a lead having a distal portion and a proximal portion, the distal portion having first and second electrodes presented therewith, and a screw portion presented at the distal portion, the screw portion extending from a tip of the lead at the distal portion and extending past the first and second electrodes towards the proximal portion.

BRIEF DESCRIPTION OF THE DRAWINGS

FIG. 8A is a schematic view of the triangle of Koch, with transitional cells ("TCs") omitted from the schematic for clarity. Interatrial septum ("IAS") pacing was delivered from the location marked with a box [1]. The roaming electrode was moved throughout the triangle of Koch, to the locations marked with additional boxes. Locations of bipolar electrodes are marked with small circles, and approximate locations of entry to the fast pathway ("FP") and slow pathway ("SP") are depicted;

FIG. 8B is a bar graph illustrating results for when 0.5-ms unipolar pulses increasing in amplitude from 0.33 to 10 mA were applied from the roaming electrode of FIG. 8A; 2-ms bipolar IAS pacing was constant at 2.times. threshold (.about.2 mA). Each ramp pulse was applied 45-60 ms before an IAS pacing pulse;

FIG. 15 illustrates a dissection of a human AV junction and creation of 3D reconstruction;

FIG. 17 illustrates Cx43 density in the AV node;

FIG. 18 illustrates Cx43 density in the His bundle;

FIG. 19 illustrates a cellular expression of Cx43;

FIG. 22 illustrates a 3D reconstruction of the AVJ conduction system; and

FIG. 23 illustrates a Cx43 quantification.

FIG. 24 depicts a clinical data table, Table 1.

DETAILED DESCRIPTION OF THE DRAWINGS

Figure 1:
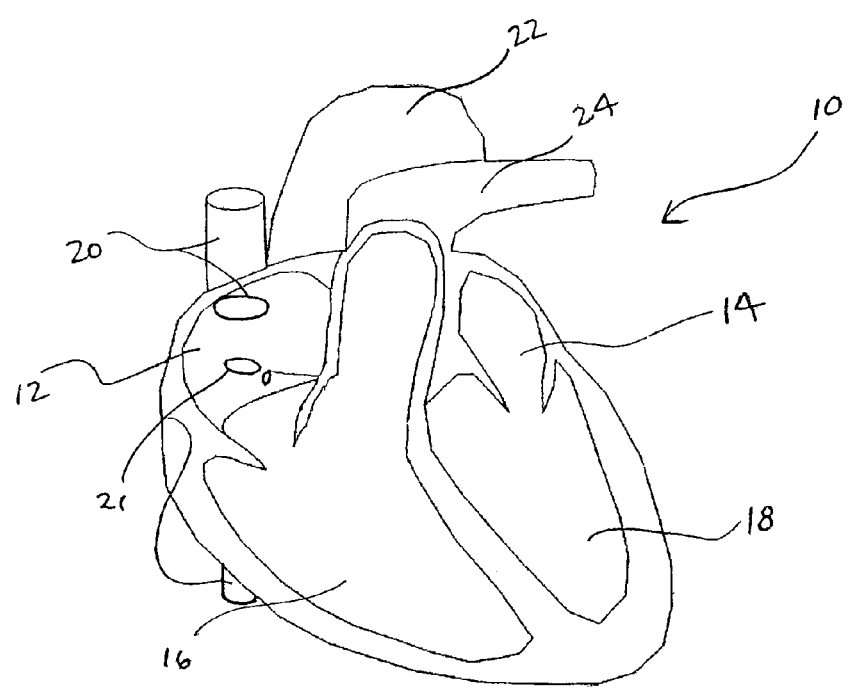
FIG. 1 is cross-sectional view of a heart.

A human heart 10 is depicted in FIG. 1. FIG. 1 depicts the following structures of heart 10: RA 12, left atrium ("LA") 14, RV 16, left ventricle ("LV") 18, superior vena cava ("SVC") 20, inferior vena cava ("IVC") 21, aortic arch 22, and pulmonary artery 24.

Figure 2:
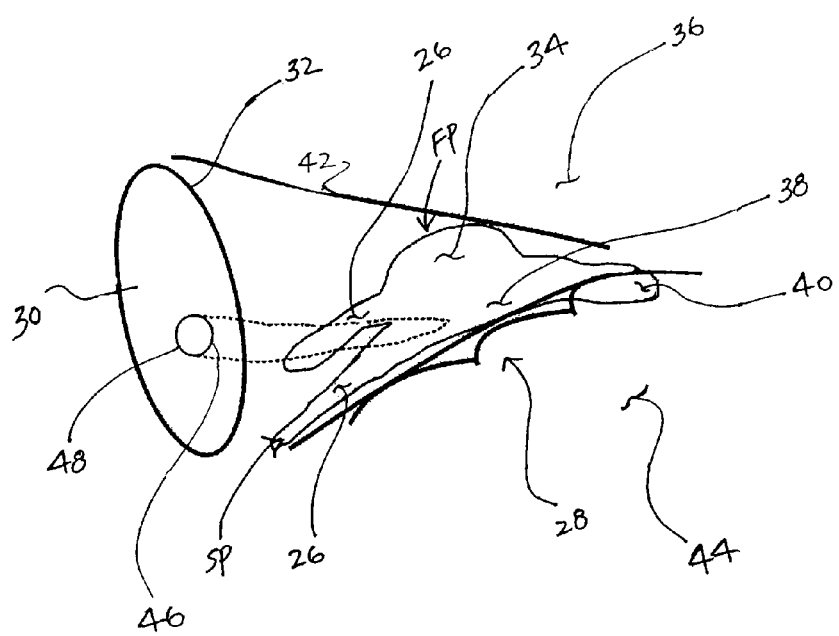
FIG. 2 is a close-up schematic view of a portion of the heart of FIG. 1, including the triangle of Koch.

Referring to FIG. 2, the following structures are depicted in a close-up view of a portion of heart 10: INE 26, tricuspid annulus 28, coronary sinus ("CS") 30, CS ostium 32, compact AV node 34, interatrial septum 36, lower nodal bundle 38, His bundle 40, tendon of Todaro 42, and ventricular septum 44. Another structure depicted in phantom lines in the heart 10 is AV nodal vein 46 and an ostium 48 thereof, which can provide an approach to INE 26 through AV node 34 via CS 30.

Referring again to FIG. 2, AV node 34 has at least two inputs which connect AV node 34 to the surrounding atrial myocardium, each with unique electrophysiological properties: the FP and the SP/INE. The FP input to AV node 34, which lies near the apex of the triangle of Koch in the RA 12, has a relatively fast conduction velocity and long refractory period. The SP input, on the other hand, is located near the tricuspid valve in the isthmus between the tricuspid annulus 28 and the coronary sinus ostium 32 in the RA 12. The SP possesses a relatively slow conduction velocity and relatively short refractory period. The distinct functional characteristics of the FP and SP are clinically manifested as AV nodal reentrant tachycardia ("AVNRT").

The coupling of the INE 26 to the His bundle 40 enables the exploitation of this connection to achieve His bundle 40 excitation without engaging the compact AV node 34. As depicted in FIG. 2 and as discussed in further below with respect to FIG. 5, an approach to the INE exists through AV nodal vein 46 via the CS 30, thereby reducing difficulties that can be associated with electrode placement. In some cases, the AV nodal vein 46 opens directly to the triangle of Koch.

Cardiac Pacing Using INE

The INE can be electrically stimulated to produce synchronized ventricular contractions via the normal conduction system of the heart. Excitation produced by pacing of the INE bypasses the compact AV node of the heart via the connexin 43-positive lower nodal bundle and thus can be used in some patients with AV block. Specifically, by using the INE as a site for placement of a pacing electrode, restoration of AV conduction in patients with various degrees of AV block can be accomplished. In addition, use of the INE as a site for placement of a pacing electrode enables normal synchronous excitation via the specialized conduction system of the heart.

In pacing the INE, advantages include that a pacing lead does not have to be passed through any valves in the heart, which can otherwise reduce the effectiveness of the valve functionality. Further, with respect to synchronized ventricular contractions, positioning a pacing lead on the left side of the heart is not required.

Also, pacing INEs can solve the problem of the electrical and mechanical asynchrony that can be associated with conventional RV and biventricular pacing. The synchronous ventricular contraction produced by INE pacing can be used to reduce the potential for pacing-induced heart failure in patients.

The existence of the INE/SP "bypass tract" in the RA enables using the INE for long-term, synchronized pacing. Locating the pacing site can be straightforward for at least the following reasons: (1) the INE/SP has a unique electrogram signature, which can be used to guide the electrophysiologist during lead implantation, (2) because the INE/SP has been a preferred target for ablation of AVNRT, electrophysiologists have already developed the tools necessary to locate it, and (3) INE/SP capture can have a higher threshold than the surrounding atrial tissue, which can be used to differentiate INE/SP capture from capture of atrial tissue.

Also, pacing from the INE/SP can have several advantages over direct His bundle pacing: (1) a relatively large area of the RA can be paced to activate the INE/SP, which can alleviate the difficulty of pacing the small His region located close to aorta, (2) INE/SP pacing can be used to avoid RVOT pacing, (3) INE/SP pacing can have lower pacing thresholds than that required for His bundle pacing due to the fibrous tissue surrounding the His bundle, and (4) INE/SP pacing can leave the normal AV node conduction pathway untouched while achieving a synchronized ventricular contraction, thus avoiding potential tissue damage that direct His bundle pacing can entail, and (5) the venous approach to the INE/SP can provide a stable lead placement site, reducing the number or lead dislodgements seen with direct His bundle pacing. As an example, in patients with intermittent AV block, INE/SP pacing can be a therapeutic solution, enabling the natural pacemaking and conduction system to pace the heart when it can and pacing the INE/SP to achieve a synchronized ventricular contraction when needed.

Figure 3:
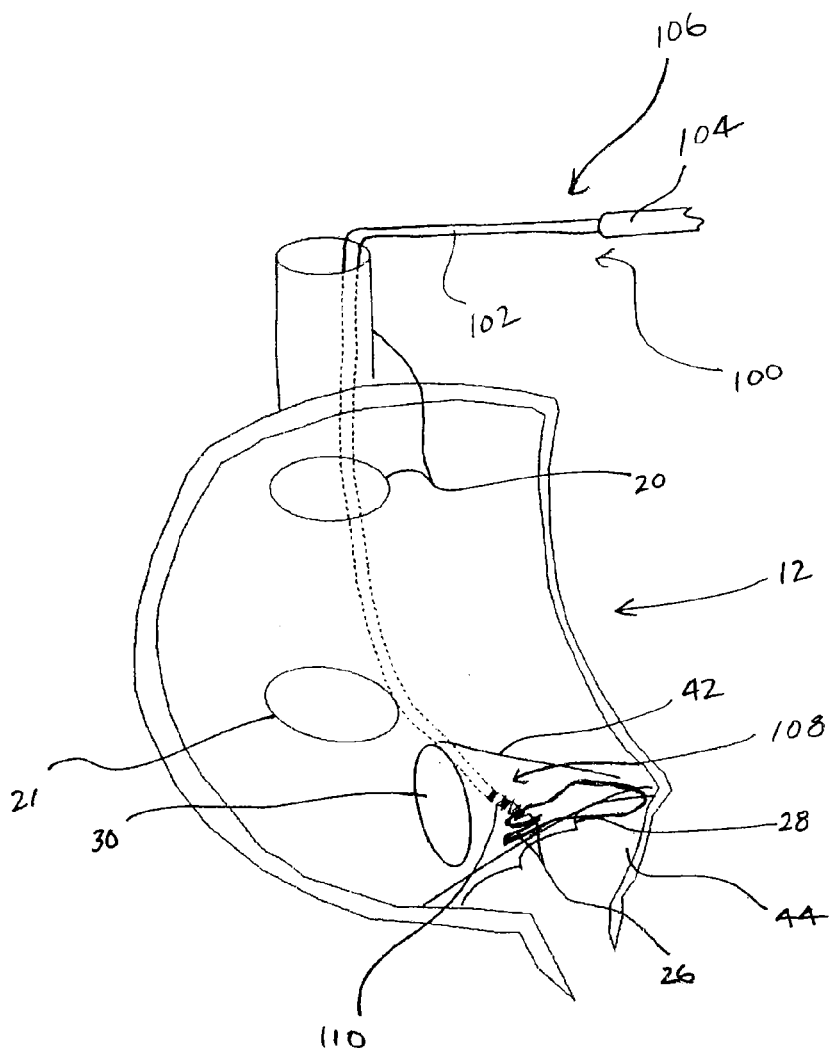
FIG. 3 depicts an endocardial approach to the INE, wherein a pacing lead according to a first embodiment is depicted partially in phantom lines.
Figure 5:
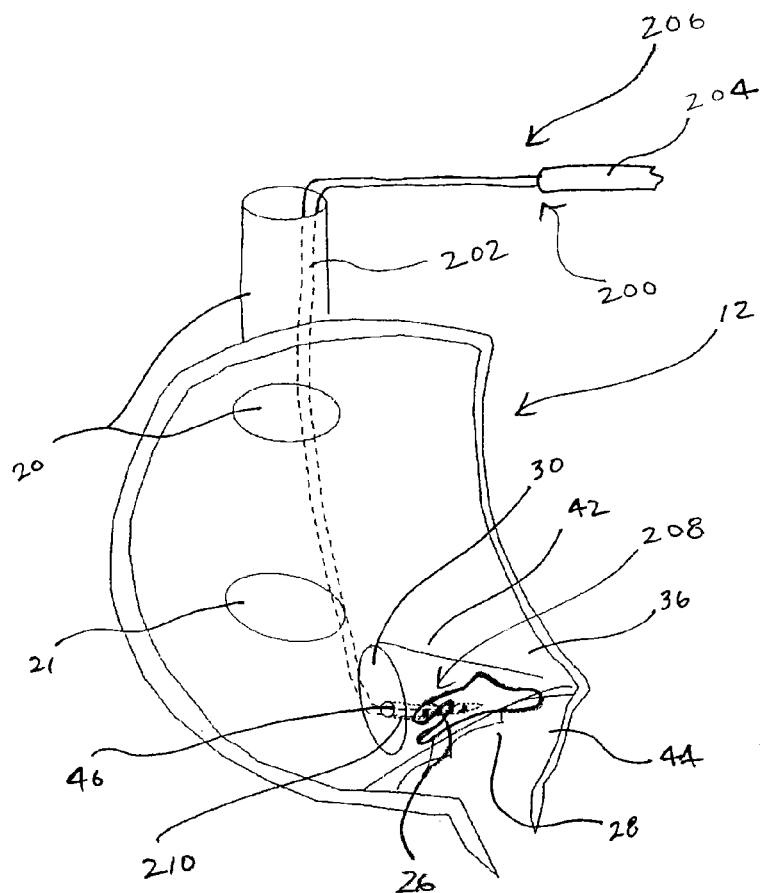
FIG. 5 depicts a venous approach to the INE, wherein a pacing lead according to a second embodiment is depicted partially in phantom lines.

As discussed in detail herein, such as with respect to FIGS. 3 and 5, there are several approaches to the INE, such as an endocardial (FIG. 3) and venous (FIG. 5) approaches. Various venous and atrial pacing leads and electrodes that can be used with INE pacing according to the various embodiments are described in U.S. Pat. Nos. 6,745,081, 6,094,596, 6,085,119, 6,070,081, 5,545,204, 4,136,703, and 3,729,008, and PCT Publication Nos. WO 2006/042295 and WO 96/10961, all of which are incorporated herein by reference in their entirety. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

Referring to FIG. 3, a first approach to the INE is endocardial. A device 100 comprises a lead 102 and a catheter 104. Lead 102 comprises a proximal portion 106 and a distal portion 108. Catheter 104 and distal portion 108 of lead 102 are inserted into the RA through the SVC. A tip 110 of lead 102 can be inserted, such as by screwing, into atrial tissue above INE 26. The insertion site in the atrial tissue can be within an anatomically effective distance to provide stimulation to an inferior nodal extension, such as within 5 mm to about 6 mm of the tricuspid valve within the triangle of Koch of the heart for humans. In embodiments, the insertion site in the atrial tissue can be within about 3 mm of the INE 26 for humans. In other embodiments, the insertion site in the atrial tissue can be within about 5 mm of the INE 26 for humans. Those skilled in the art will recognize that insertion site in the atrial tissue can be more than about 5 mm or less than about 3 mm of the INE. Once lead 102 is inserted into atrial tissue above INE 26, catheter 104 can be withdrawn or remain with lead 102. The INE of the human, as well as the venous approach to the INE, is discussed in further detail in Hucker et al., "Connexin 43 Expression delineates two discrete pathways in the human atrioventricular junction," Anatomical Record 2007, attached as Appendix A hereto, which is incorporated herein by reference in its entirety.

Figure 4:
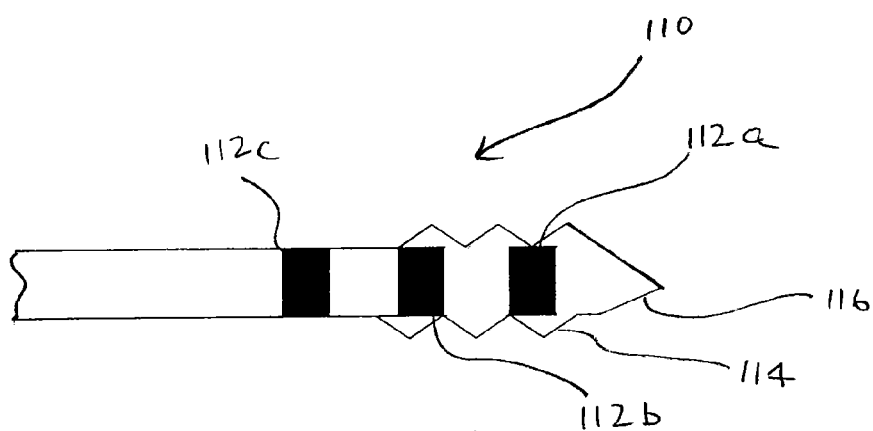
FIG. 4 is a close-up view of a tip of the lead of FIG. 3.

Referring to FIG. 4, lead tip 110 in this embodiment can include first, second, and third electrodes 112a, 112b, 112c and a screw portion 114 surrounding the distal-most two electrodes 112a, 112b. Lead tip 110 can further include a point 116, which can be inserted into the atrial tissue for pacing and sensing the INE. Lead tip 110 can then be screwed into atrial tissue above the INE 26 by effecting a screwing motion of lead tip 110 such that screw portion 114 drives lead tip 110 into atrial tissue. Third electrode 112c can be used for far field sensing of ventricular contractions.

To achieve long term pacing with this approach, screw portion 114 can be about 2.0 mm to about 3.0 mm long and can surround pacing and optionally sensing electrodes. The pacing electrodes (such as 112a, 112b) can be buried within the atrial tissue. Those skilled in the art will recognize that greater than or fewer than three electrodes can be included on pacing lead 102. Those skilled in the art will also recognize that screw portion 114 can be shorter than about 2.0 mm and longer than about 3.0 mm or that other alternatives for securing lead tip 110 to INE 26 pacing site can be used.

An AV nodal vein approach is depicted in FIG. 5. A device 200 comprises a lead 202 and a catheter 204. Lead 202 comprises a proximal portion 206 and a distal portion 208. Specifically referring again to FIG. 2, an approach to INE 26 exists through AV nodal vein 46 via the CS 30. In some cases, AV nodal vein 46 opens directly to the triangle of Koch. Catheter 204 and distal portion 208 of lead 202 are inserted into the RA 12 through SVC 20, into CS 30 through ostium 32 of CS 30, and into AV nodal vein 46 to INE 26. A tip 210 of lead 202 in this embodiment can comprise first, second, third, and fourth electrodes 212a, 212b, 212c, 212d.

There are catheter insertion methods and designs that enable navigating the CS and inserting the catheter and lead into the heart. Such insertion methods are described in U.S. Pat. Nos. 6,745,081, 6,070,081, and 5,545,204, which are incorporated herein by reference in their entirety. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The catheter design of the embodiments can differ from conventional catheter designs in that it can be shorter than those used for epicardial pacing and can be steerable enabling the catheter tip to enter the AV nodal vein. For example, to facilitate entry into the AV nodal vein, the tip of the catheter can have a slight bend, such as between about 10.degree. and about 60.degree. Those skilled in the art will recognize that in further embodiments the tip of the catheter can have a bend less than about 10.degree. and greater than about 60.degree.

Figure 6:
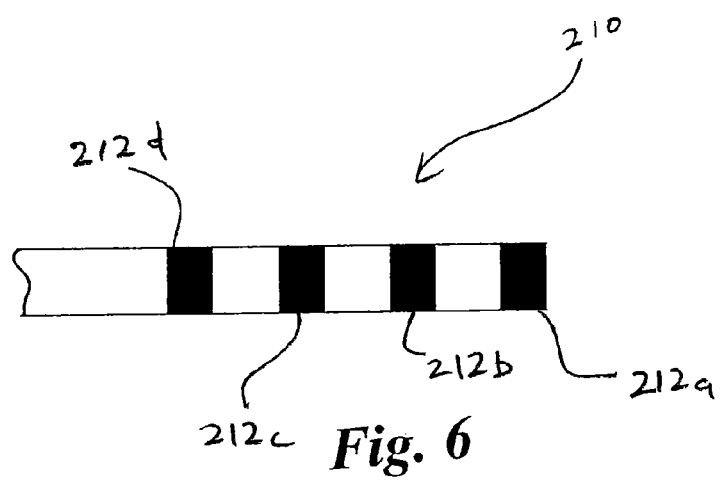
FIG. 6 is a close-up view of a tip of the lead of FIG. 4.

Referring again to FIGS. 4 and 6, lead tip 110, 210 according to embodiments can comprise multiple electrodes (depicted as having three and four electrodes, respectively), which can be switched from sensing to pacing. Those skilled in the art will recognize that in further embodiments, greater than four or fewer than three electrodes can be included on the lead tip. Unipolar sensing on each lead can be used to determine which lead has the most robust slow pathway signal. The lead can then be switched to be the pacing lead and SP pacing can be accomplished with this lead. The non-pacing leads can then be used to monitor ventricular rate during pacing, which can be done in bipolar mode.

Figure 7:
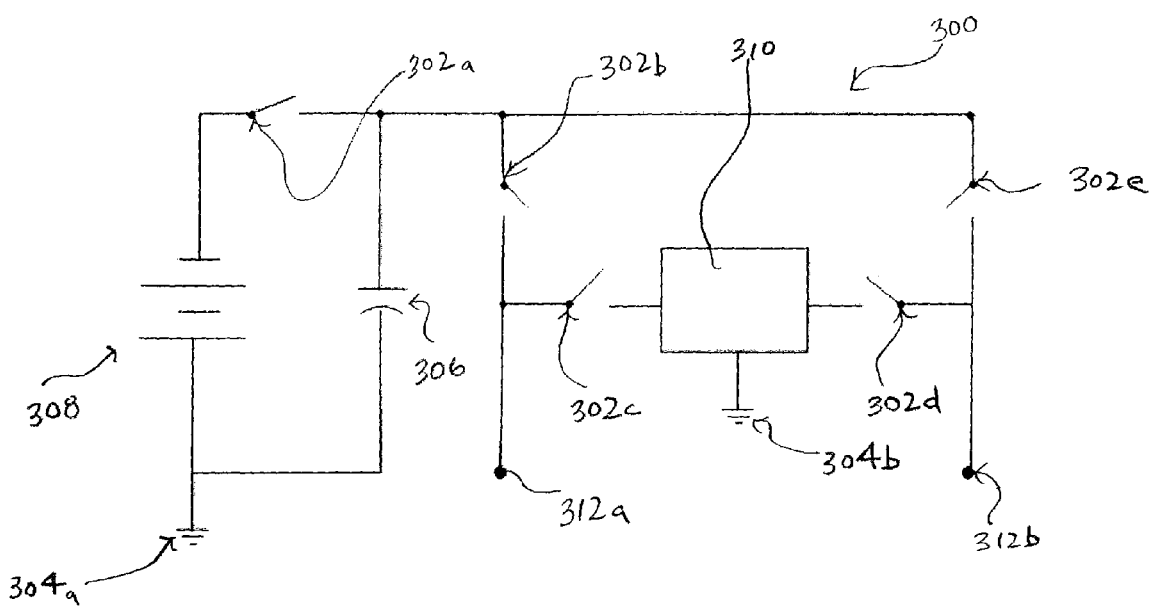
FIG. 7 is an electrical diagram for an electrode according to a third embodiment.

The circuit diagram in FIG. 7 illustrates an embodiment of how each lead electrode of a lead 300 can be switched from a pacing function to a sensing function. Two leads electrodes 312a, 312b are depicted in the diagram for clarity. Circuit 300 comprises a plurality of switches 302a, 302b, 302c, 302d, 302e, a first ground 304a and a second ground 304b, a capacity 306, a battery 308, electrocardiogram ("ECG") sensing circuitry 310, and a plurality of electrodes 312a, 312b.

When switch 302a is closed, the capacitor can charge, and when switch 302a is open, capacitor 306 is disconnected from battery 308. With switches 302c and 302d closed, a unipolar ECG can be sensed from both lead 312a and lead 312b with the reference lead for ECG sensing circuitry 310 being the can of the device. ECG sensing circuitry 310 decides which lead has the best slow pathway ECG. Then switches 302c and 302d open and switch 302b or 302e, which are controlled by ECG sensing circuitry 310, close to connect lead with the best slow pathway potential to capacitor 306 for unipolar pacing. Those skilled in the art recognize that electrical stimulation can be delivered in any number of ways electronically and in any number of wave shapes, frequency, voltage, and timing.

Synchronized ventricular pacing is described further in Hucker et al., entitled "Atrio-Ventricular Conduction with and without AV Nodal Delay: Two Pathways to the Bundle of His in the Rabbit Heart," Am. J. Physiol. Heart Cir. Physiol. October 2007; 293(2):H1122-30, which is incorporated herein by reference in its entirety.

EXAMPLES

Setup

New Zealand White rabbits (n=18, 2.5-3 months old, 2-3 kg) were anesthetized with 100 mg/kg pentobarbital sodium and 1,000 IU heparin intravenously, after which a midsternal thoracotomy was performed and the heart removed. The heart was Langendorff perfused with oxygenated (95% $O_2$-5% $CO_2$) Tyrode at 37.degree. C. and received 50.mu.1 of 5.mu.M Di-4-ANEPPS (Molecular Probes, Eugene, Oreg.) over 5 minutes. The study was conducted in superfused isolated AV junctions (n=8) and in Langendorff-perfused hearts (n=10) with the AV junction exposed via right atriotomy. For superfused experiments, the AV junction was dissected in cold Tyrode (0.degree. C.) and the sinoatrial node was removed. The preparation was superfused at 30 ml/min with Tyrode containing 15 mM of the excitation-contraction uncoupler 2,3-butanedione monoxime (Sigma, St. Louis, Mo.) to inhibit motion artifacts. A 16.times.16 photodiode array was used with an optical mapping system. Optical signals were sampled at 1.5 kHz, averaged, and low-pass filtered at 120 Hz. Optical activation maps displayed the optical signal derivative, which corresponds to wave fronts of excitation.

Electrogram Recordings

Electrodes were placed on the IAS and CrT, and a quadruple electrode on the His bundle recorded both the superior and inferior His electrogram (SHE and IHE, respectively) to monitor fast-His and slow-His excitation.

Changes in His excitation and His electrogram morphology can occur from changes in the AV node excitation pathway, because of the specific pacing protocol and alternating conduction pathways. If the AV node and His are excited by the SP (i.e., slow-His excitation), the IHE has a larger amplitude than when the AV node is activated by the FP. Conversely, when the FP excites the AV node and His (i.e., fast-His excitation), the SHE has a larger amplitude than with slow-His excitation.

The location of each electrode is depicted in FIG. 8A. A fourth roaming electrode was used to record electrograms throughout the triangle of Koch. A schematic of the triangle of Koch is depicted in FIG. 8A. The reference lead was located 3 mm from the electrode tip. The TEFLON®-coated 0.13-mm Pt/Ir wire tip had .about.0.07 mm stripped to mimic a clinical hemispheric tip. This electrode was mounted on a force transducer (FORT25; World Precision Instruments, Sarasota, Fla.) to control contact force, ensuring that contact force was minimal and consistent between locations. The roaming electrode was moved in 1-mm increments by a motorized micromanipulator throughout the triangle of Koch (grid in FIG. 8A). Electrograms were recorded at 1.5 kHz (National Instruments, Austin, Tex.), and each electrode location was digitally photographed.

Stimulation Protocol

The preparation was paced from two electrodes: the IAS electrode and the roaming electrode (FIG. 8A). IAS pacing was constant at 2.times. threshold (.about.2 mA), with 2-ms pulses and 300-ms cycle length (FIG. 8B). IAS pacing simulated sinus pacing and was used to mask the AV junctional rhythm, which originates in the SP, as well as to maintain tissue excitability in a consistent state as the roaming electrode was moved from location to location. Stimulation thresholds were determined with a ramp of unipolar pulses (0.5-ms pulses, 300-ms cycle length, amplitude ranging from 0.33 to 10 mA and increasing by 0.33 mA with each pulse; FIG. 8B). Each ramp pulse was delivered 45-60 ms before an IAS pacing pulse (FIG. 8B). The pacing ramp was delivered from the roaming electrode for anywhere from 14-24 locations throughout the triangle of Koch (grid in FIG. 8A), enabling quick determination of threshold for each location. Pacing threshold was defined as the amplitude of the ramp pulse that caused a shift in the activation pattern from IAS pacing to stimulation beginning from the roaming electrode.

Results—Identifying the SP

The schematic in FIG. 8A indicates the approximate location of the inputs to the SP and FP. Although the anatomic substrate of the SP is often thought to be the INE, the anatomic substrate of the FP is less well defined and consists of TCs that overlay the compact AV node.

Figure 9:
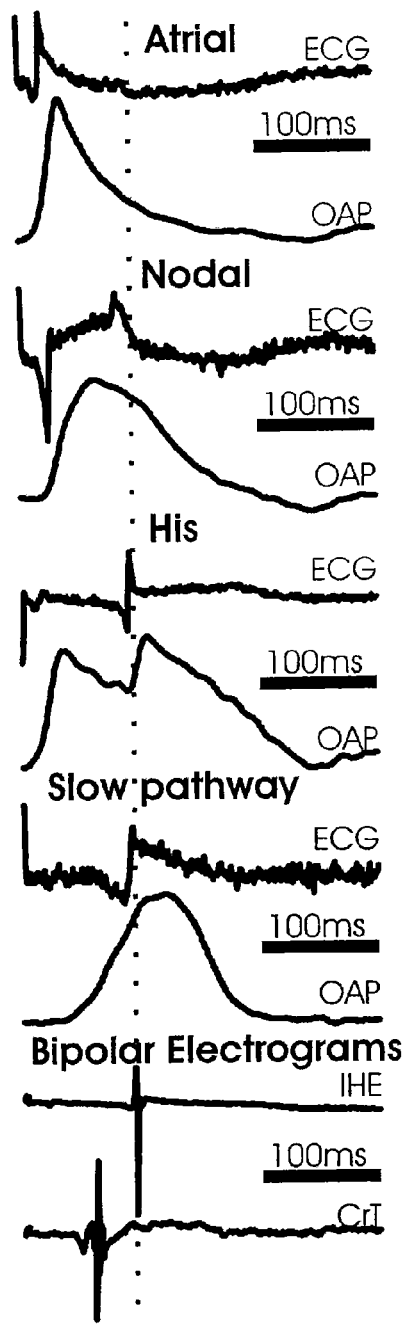
FIG. 9 is a comparison of selected electrograms and optical action potentials ("OAPs") recorded from the same site for atrial tissue, His, nodal, SP, ventricular, and intermediate traces, with the dotted line marking the time of the bipolar inferior His electrogram ("IHE") trace (each trace being 300 ms long)

Electrograms and OAPs were compared that were recorded during IAS pacing. Each trace began at the moment of IAS pacing and was 300 ms long. FIG. 9 directly compares electrograms and OAPs recorded from the same site. During IAS pacing, the AV node is activated by the FP, and the SP acts as a dead-end pathway. Electrograms for atrial tissue all have a sharp signal immediately after the pacing artifact, which signifies fast conduction through the atrial myocardium. OAPs for atrial tissue have atrial action potential morphology. Electrograms for His contain both a fast signal directly after the pacing artifact (similar in timing to that seen in traces for atrial tissue) and another sharp spike .about.80 ms later, which reflects His excitation. OAPs for His have two humps that are the summation of atrial and His excitation. The first hump corresponds to atrial activation, whereas the second hump has the distinct plateau phase of His activation. Electrograms for nodal and SP contain several components. The first component matches in time the signals seen in the electrogram for atrial tissue and is followed by complex low-amplitude biphasic recordings that are consistent with slow conduction during the interval between atrial and His excitation. Electrograms for nodal are located near the anatomic location of the AV node, and OAPs for nodal have a nodal morphology. Electrograms and OAPs for SP are located along the SP. There is overlap in the characteristics of the electrograms and OAPs for nodal and SP.

Referring again to FIG. 9, the sharpest spikes in the electrograms correspond to the dF/dtmax of the fluorescent optical signals. In the nodal and SP traces, the slow conduction characteristics of the electrograms correlate well with the OAPs from the same location. One exception is the spike seen in the nodal electrogram, which occurs during the plateau of the OAP. On the basis of the timing of this spike relative to the bipolar IHE, this spike most likely reflects excitation of the nodal-His (NH) region of the node or the lower nodal bundle (LNB), where excitation accelerates into the His bundle.

Pacing stimuli applied within the triangle of Koch produced different activation patterns, depending on where the stimuli were delivered. The activation pattern caused by IAS pacing originated from the IAS electrode and spread rapidly across atrial tissue and TCs that lie above the conduction system in the triangle of Koch, which activated the FP of the AV node. Because activation maps display dF/dt, there is no conduction visible from .about.50 to 70 ms when there is exclusively slow AV node conduction (which has a low amplitude dF/dt). After this period, His excitation occurred, which actually began in the LNB region. The interval between IAS pacing and His excitation was ~70 ms.

At many pacing locations within the triangle of Koch, pacing from the roaming electrode caused an atrial/FP activation pattern similar to that seen with IAS pacing.

When the roaming electrode was placed within ~2 mm of the tricuspid valve within the triangle of Koch, it excited the SP. SP activation appears as a slow, narrow activation pattern that moved toward the apex of the triangle of Koch. After it reached the AV node region, excitation continued toward the His bundle without pause and also spread retrogradely across the IAS. In the SHE trace, the His electrogram morphology changed to a slow-His morphology with a smaller amplitude during SP pacing and returned to its original morphology after the ramp ended. The interval between stimulation and His excitation (the S—H interval) is paradoxically longer for fast-His excitation than for slow-His excitation. Slow-His electrograms were observed in six of eight superfused experiments.

Figure 10:
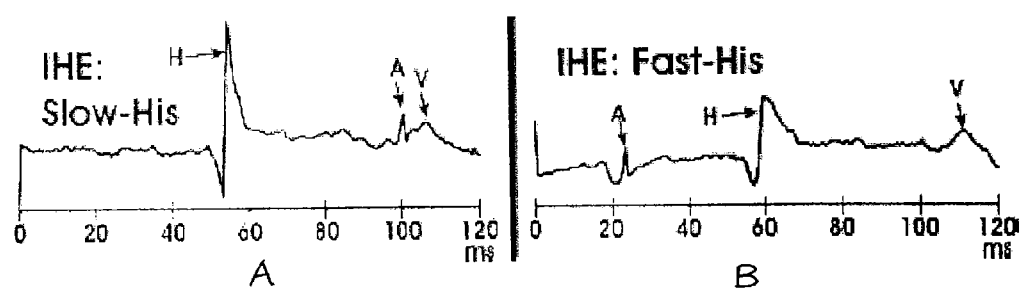
FIG. 10A is a superior His electrogram ("SHE") trace corresponding to SP pacing from a roaming electrode located on the SP (SP electrode) producing SP and His excitation—A, H, V representing atrial, His, and ventricular components of IHE, respectively.
FIG. 10B is a SHE trace corresponding to IAS pacing of the high IAS first excited atrial tissue—A, H, V representing atrial, His, and ventricular components of IHE, respectively.

Similar optical activation patterns for SP and atrial/FP activation were observed in the AV junctions of Langendorff-perfused hearts. An IHE trace for activation maps of SP pacing is depicted in FIG. 10. SP pacing in the whole heart produced a slow narrow activation pattern followed without pause with His activation. In the intact heart, His activation was followed by a robust ventricular optical signal that could be seen through the overlying atrial tissue. Atrial activation preceded ventricular activation by ~10-15 ms.

IAS pacing produced a fast wave of excitation that spread across the atrial tissue and TCs. After atrial activation, excitation spread from the AV node region in two directions: the wave front of His excitation spread toward the His electrode and a wave front of decremental conduction spread down the SP and died out. Ventricular activation followed His excitation. A small amplitude fast-His potential is seen in FIG. 10 for IHE with IAS pacing (i.e., the IHE deflection is larger with SP pacing than with IAS pacing).

Pacing within the Triangle of Koch

FIGS. 9-10 illustrate that the SP location can be identified with electrograms and OAP morphology, and SP vs. FP activation can be differentiated with activation patterns and His electrogram morphology in both the superfused and whole heart preparations. Using both activation patterns and His morphology, it was identified which activation patterns occurred for multiple pacing locations throughout the triangle of Koch.

Figure 11:
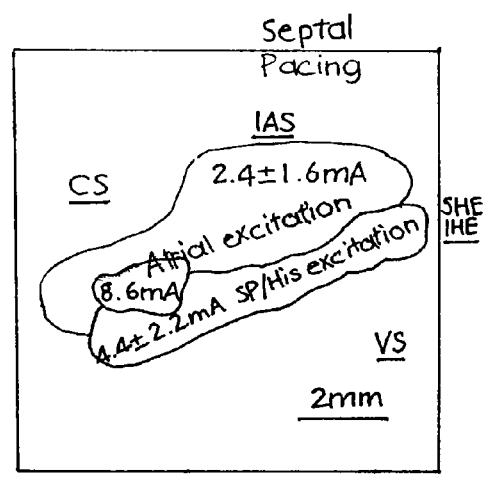
FIG. 11 is a summary plot of activation patterns and stimulation thresholds throughout the triangle of Koch from 8 superfused experiments, wherein the box marks optical mapping field of view.

FIG. 11 displays a summary of where the different activation patterns occurred and the pacing thresholds in the superfused experiments. Generally, pacing stimuli applied within about 2 mm of the tricuspid valve excited the SP or the His directly when pacing near the apex of the triangle of Koch. Direct His stimulation was defined as fast conduction directly after stimulation, which had an S—H interval of ~10 ms and occurred in a small area near the His electrode. On average, the pacing threshold for SP/His pacing was 4.4±2.2 mA. Pacing stimuli applied further away from the tricuspid valve generally excited atrial tissue, producing FP excitation of the AV node with an average stimulation threshold of 2.4±1.6 mA ($P<0.001$ compared with SP/His pacing thresholds). Additionally, there was one area between the coronary sinus and the tricuspid valve that had very high pacing thresholds (8.6±1.4 mA; $P<0.001$ compared with atrial/FP thresholds). Pacing this region excited atrial tissue and the FP of the AV node. OAPs from this region were quite noisy and very dissimilar from the large-amplitude atrial OAPs recorded from other areas of the triangle of Koch. High pacing thresholds and very low OAP amplitudes suggest that few excitable cells are located in this region. There were several instances where different activation patterns occurred at different thresholds, typically with atrial activation followed by SP or His excitation at higher stimulus intensities. Very similar pacing thresholds for each activation type were observed in the Langendorff-perfused hearts with the SP/His threshold statistically the same as the right ventricular pacing threshold.

Figure 12:
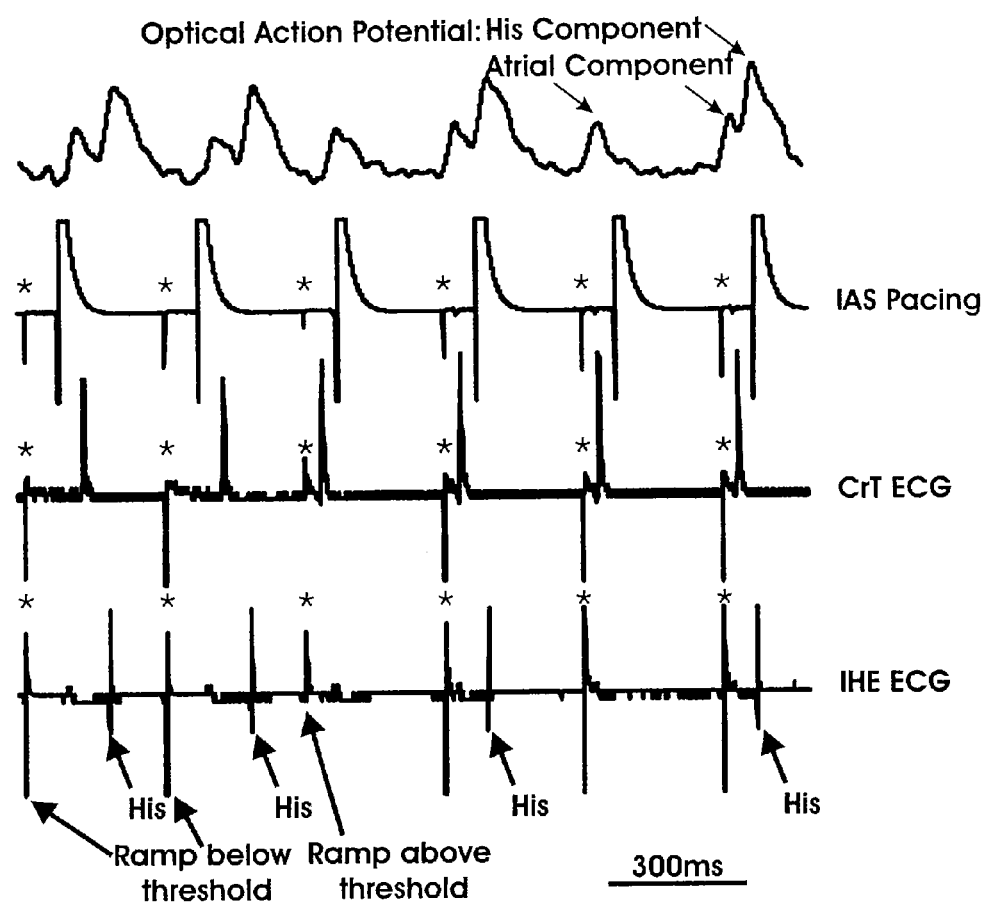
FIG. 12 is an OAP recorded from the area proximate the IHE and electrograms from IHE, crista terminal ("CrT"), and IAS pacing electrodes, wherein ramp artifacts, which differ due to aliasing (0.5-ms pulses sampled at 1,500 samples/s). Before the ramp is above threshold, the preparation is paced from the IAS. When the ramp is above threshold, 2:1 AV block occurs.

Once SP activation of the His bundle has occurred, the SP would excite the His bundle throughout the duration of the stimulation ramp in a 1:1 fashion. However, this was not the case for all pacing locations that produced FP excitation. As depicted in FIG. 12, pacing near the superior border of the AV node often disrupted AV conduction by causing 2:1 AV block or prolonged AV conduction. In the example depicted in FIG. 12, IAS pacing conducted 1:1 to the His before the stimulation ramp crossed threshold, seen in both the electrograms and the OAP recorded above the His bundle. Once the stimulation ramp crossed threshold, it excited atrial tissue (seen in the shift in both the OAP and the CrT trace), but excitation did not propagate to the His. In the next beat, excitation propagates to the His (seen in the OAP and the IHE), and conduction continues in this 2:1 fashion. Therefore, AV conduction was disrupted by pacing in this location. Pacing stimuli delivered to this area of the triangle of Koch caused 2:1 AV block or prolonged AV conduction in five of eight experiments. Once AV conduction was disrupted, it did not fully recover in any of the five experiments, suggesting that the effect of pacing in this area was not neurologically mediated. The S—H interval was measured for each pacing location.

Figure 13:
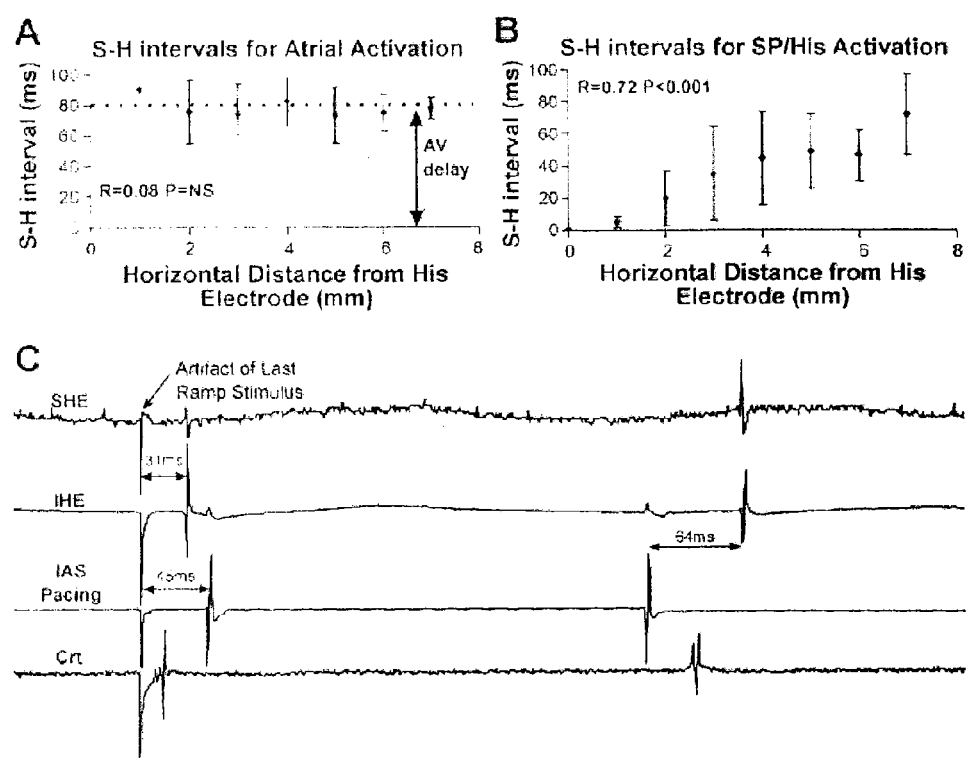
FIG. 13A is a graph illustrating intervals between stimulation and His excitation (S—H intervals) associated with atrial/FP activation.
FIG. 13B is a graph illustrating intervals between stimulation and His excitation (S—H intervals) associated with SP and His activation for all superfused experiments are plotted vs. the distance from the His electrode.
FIG. 13C illustrates electrograms recorded at the end of a stimulation ramp, which excited the SP, and the following beat, which was paced from the IAS. The unipolar ramp generated a much larger stimulus artifact in the electrograms than bipolar IAS pacing.

The S—H interval usually stabilized three to five pulses after threshold was reached, and these stable values were measured. S—H intervals at high-stimulus intensities, where a greater amount of tissue was presumably depolarized by far-field stimulation, were discarded because the S—H intervals at the end of the ramp were generally different from the stable S—H intervals. Rarely, S—H intervals did not stabilize and linearly decreased throughout the ramp, in which case the range of S—H intervals was noted. Also, any S—H interval that was recorded after AV conduction was disrupted was discarded from the analyses, as depicted in FIG. 12. S—H intervals were divided into two groups, those associated with atrial/FP activation and those associated with SP/His activation. When plotted against the horizontal distance from the His electrode, atrial S—H intervals illustrated no distance dependence (P=not significant; FIG. 13A) but instead remained at a constant level of 81±19 ms. This constant interval between an atrial stimulus and His excitation is the AV delay. S—H intervals associated with SP and His excitation exhibited a strong correlation with distance from the His electrode ($P<0.001$; FIG. 13B). If SP excitation experienced the AV delay, one would expect a nonlinear jump from direct His excitation at small distances from the His electrode to values at or above the AV delay of 81±19 ms. Moreover, the S—H intervals during SP pacing remained well below the AV delay measured from atrial/FP activation (81±19-ms delay for FP excitation and 53±25-ms delay for SP excitation.g-toreq.4 mm from the His electrode; P<0.001).

FIG. 13C depicts an example of S—H intervals measured during SP pacing and IAS pacing with the last ramp stimulus, which excited the SP, and the first IAS pacing pulse after the ramp. The S—H interval was 31 ms for the last ramp stimulus and increased to 64 ms when the His bundle was excited by IAS pacing. Paradoxically, the S—H interval for the SP was shorter than the S—H interval for the FP. The shifts from slow-His to fast-His potentials are seen in both the IHE and SHE traces. Similar S—H interval trends for both atrial and SP excitation were observed in Langendorff-perfused hearts, with SP S—H intervals shorter than FP S—H intervals on average Discussion The results support previous findings that several layers of conduction exist in the triangle of Koch. Now, it was further demonstrated that these layers can be differentially engaged with varying stimulus strengths and pacing locations. It was found that stimulation thresholds for atrial excitation are significantly lower than for SP/His activation, with the exception of one area beneath the coronary sinus. Using the activation pattern documented by optical mapping, as well as slow-His electrograms, SP excitation was verified and it was found that not only do S—H intervals decrease linearly as the stimulus location approaches the His bundle for SP excitation, whereas S—H intervals associated with atrial/FP activation remain nearly constant, but also that paradoxically S—H intervals for the SP are shorter than those recorded for FP activation.

Because of the different modalities used to study the AV junction, there is a "lack of common terminology" for its components. For instance, many previous studies have referred to the AV node extension located in the isthmus between the coronary sinus and the tricuspid valve as the "posterior nodal extension." However, a naming task force has indicated that the INE more accurately describes its location when the heart is anatomically oriented. Previous studies have described layers of atrial cells and TCs overlying the components of the conduction system in the triangle of Koch, such as the INE, AV node, and His bundle. Functional studies have provided evidence that the INE is the anatomic substrate of the SP. However, there is debate regarding whether the INE itself, the TCs overlying the INE, or a combination is the true substrate of the SP. The results can not distinguish which cell layer or structure produced SP excitation. However, optical mapping results confirm that this pathway can be reliably excited by pacing stimuli delivered within ~2 mm of the tricuspid valve within the triangle of Koch. Plotting S—H intervals of atrial excitation against the distance from the His electrode revealed no correlation (FIG. 13A). The S—H interval of atrial activation is composed of two intervals: conduction time in the atrial layer and FP (S-AV node interval) and AV node conduction to the His bundle (the AV delay). Because conduction in the atrial layer is fast (~35 cm/s), small changes in the distance between the stimulating electrode and the His electrode change the S-AV node interval minimally. Therefore, the main determinant of the S—H interval is the AV delay, which remains essentially constant.

On the other hand, plotting S—H intervals of SP excitation vs. distance from the His electrode illustrated a strong correlation (FIG. 13B). A greater dependence on distance would be expected for SP activation because, as the name implies, the SP conducts slowly (.about.7 cm/s). Therefore, one would expect the S-AV node interval to decrease slightly as the distance between the stimulus and the AV node decreased. However, once conduction time in the SP is minimal, the S—H interval should be determined by the AV delay, which is 81.+−0.19 ms according to the atrial activation data (FIG. 13A). As the His bundle is approached further, the S—H interval should then jump to a very small value when direct His activation occurs. Instead, the raw data and the pooled data in FIG. 13B depict S—H intervals almost entirely<81 ms and a linear decrease of the S—H interval as the His electrode is approached. Activation patterns for SP pacing illustrated SP excitation proceeding linearly to the His bundle without pause. These data suggest that there is no dependence of the SP/His S—H interval on the AV delay, implying that SP excitation avoids the AV delay and excites the His bundle directly.

Figure 14:
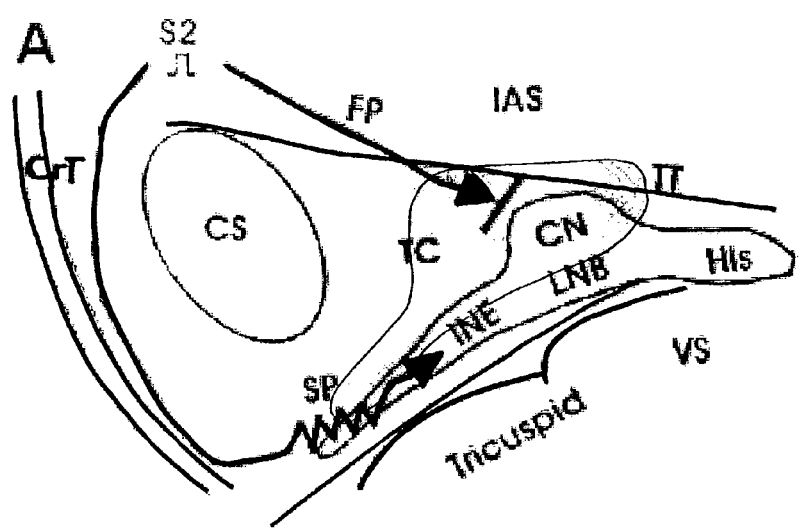
FIG. 14 is a schematic of the propagation of a premature stimulus to the His bundle through the SP

Studies have investigated the rate-dependent properties of the SP vs. the FP in the context of premature stimuli, most commonly with pacing stimuli applied in the high right atrium or to the CrT. On the basis of these studies, the SP was given its name because excitation took longer to reach the His bundle than through the FP. However, it was found that SP excitation reached the His bundle faster than FP excitation. Despite this apparent paradox, results are fully consistent with the large body of evidence concerning the SP for two reasons. First, SP excitation in previous studies traveled the full length of the SP, which data indicates would have an S—H interval similar to FP excitation (FIG. 13B, right). In the context of a premature beat, this activation would take even longer. In the absence of pacing stimuli applied directly to the SP, SP conduction to the His only occurs when a premature stimulus encounters a refractory FP (FIG. 14). Because conduction traveling the full length of the SP takes the same amount of time as the AV delay (or longer with premature stimuli), it could be difficult to recognize that SP conduction avoided the AV delay. Only through pacing the SP incrementally along its length could it become apparent that SP excitation does not experience the same AV delay as FP excitation. Second, the SP was engaged directly, potentially avoiding any conduction delay that may occur at the interface of the atrial tissue with the SP (FIG. 14). This interface may be responsible for an additional delay in conduction, which would slow SP conduction even further.

Pacing was done at 300 ms within the triangle of Koch, close to the AV node itself. Therefore, one interpretation of the data is that because of the His bundle proximity, pacing stimuli excited the His bundle directly when stimuli were delivered within 2 mm of the tricuspid annulus and the SP was not involved. Direct stimulation of the His bundle would certainly result in short S—H intervals. However, this possibility is unlikely for two reasons. First, SP activation was confirmed by being visualized with optical mapping. Second, pacing stimuli applied much closer to the His bundle itself produced atrial activation with an AV delay of .about.80 ms or longer throughout the entire pacing ramp. Therefore, it seems that the tissue area initially captured by the pacing stimulus was rather small. Also, the S—H intervals that were analyzed were measured three to five beats after the pacing ramp reached threshold (i.e., <2× the pacing threshold) which also limits the extent of tissue that was excited at that point in the pacing ramp.

There is a growing consensus in the literature that the His, LNB, and the INE form a continuous structure distinct from the compact AV node tissue on a morphological, molecular, and functional basis. The data suggests that, instead of a final common pathway as classically suggested, there are instead two pathways to the His bundle: one through the compact node and the other through the LNB. Similar arguments have been put forth suggesting that the INE connects to the His bundle through the LNB and that the FP passes through the compact node. The concept of two pathways to the His is supported by changes in His electrogram morphologies (i.e., slow-His and fast-His electrograms). The distinct His electrogram signatures of FP or SP activation indicate that the activating pathway influences how the His bundle, or which part of the His bundle, is depolarized.

Based on this dual-pathway concept, the data suggests that SP excitation begins in either the inferior TCs or the INE itself and travels via the INE to the His bundle through the LNB with a gradient of conduction velocities. As excitation approaches the His, the level of connexin 43 increases and conduction velocity increases until the His bundle is reached. FP activation from the atrial tissue surrounding the AV node funnels into the compact node via the TCs that overlie the AV node. The AV node delay is due to the compact nodal tissue and its connecting TCs, after which excitation passes to the His. Interestingly, a small region was identified below the coronary sinus where stimulation thresholds were significantly higher than the surrounding myocardium. This area may serve as a localized area of block, contributing to anisotropy in the atrial myocardium and may play a role in atrial flutter and fibrillation, similar to the block zone in the intercaval region that can maintain typical atrial flutter.

The existence of an SP "bypass tract" in the right atrium expands the area that can be paced to achieve His bundle excitation with direct His bundle pacing procedures, alleviating the difficulty of pacing the small His region located close to aorta. Locating the SP pacing location could be guided by the slow conduction characteristics in SP electrograms, such as depicted in FIG. 9, which are used to guide SP ablations during AVNRT procedures. SP pacing may very well have lower pacing thresholds than those required for His bundle pacing because of the fibrous tissue surrounding the His bundle. Experiments in the rabbit revealed that SP pacing and direct His pacing had pacing thresholds that were not statistically different. However, in the rabbit, the endocardial side of the His bundle is only covered by a small amount of connective tissue, whereas, in the human, the His bundle is encased in the fibrous tissue of the central fibrous body. Therefore, it is possible that SP pacing in the human will have a lower threshold than His bundle pacing. Additionally, pacing thresholds for right ventricular epicardial pacing and SP/His pacing were not statistically different in the whole heart experiments, suggesting that clinical SP pacing thresholds may be close to pacing thresholds for right ventricular pacing. However, this study was conducted in normal rabbit AV junction preparations where no attempt was made to disrupt AV conduction. Conduction curves are the gold standard used to investigate AV node dual-pathway electrophysiology. Because of the number of pacing locations investigated, it was not possible to construct conduction curves for each. Although conduction curves are very useful clinical tools, optical mapping in the preparations confirmed the distinct activation patterns of FP vs. SP activation, and optical mapping of SP excitation corresponds very well to SP optical mapping performed during standard S1-S2 protocols. Additionally, slow-His potentials provided another line of evidence for FP vs. SP participation in conduction.

Further description is included in Hucker et al., "Atrioventricular Conduction With and Without AV Delay: Two Pathways to the Bundle of His in the Rabbit Heart," Am. J. Physiol. Heart Circ. Physiol., 2007 August; 293(2):H1122-30, which is incorporated herein by reference in its entirely.

INE as Physiologic Pacemaker

The INE can also be used for biological pacemaker therapy. Specifically, the INE is the secondary physiological pacemaker of the heart and can be modified to become the leading pacemaker during failure of sinus nodal pacemaker. The inherent pacemaking properties of the INE can be enhanced to reach normal physiological heart rates. Specifically, the pacemaking properties of the INE can be enhanced by electric sympathetic stimulation of the elements of sympathetic branch of cardiac autonomic nervous system surrounding the myocytes of the INE.

Delivery of sub-threshold high frequency (about 20 Hz to about 400 Hz) current can be used to stimulate the endogenous autonomic innervation surrounding the INE and enable acceleration of the physiological pacemaker in the INE. Further, the pacemaking properties of the INE can be enhanced by electric stimulation of the elements of sympathetic branch of cardiac autonomic nervous system located within the myocardium of INE. Further description is included in Hucker et al., "Automatic Control and Innervation of the Atrioventricular Junctional Pacemaker," Heart Rhythm, October 2007, 4(10), pages 1326-1335, which in incorporated herein by reference in its entirely. The sub-threshold approach can replace the need for traditional ventricular pacemaker leads. Sub-threshold stimulation can be applied using the device designs described above or can be applied with other known electrode designs.

Electrical Modulation of INE

The INE can also be electrically modulated to treat several common conditions in clinical electrophysiology. For example, stimulation of the INE can be used for treatment of several cardiac rhythm disorders of supraventricular origin, including bradycardia and tachycardia, and also as a site for implantable device pacing treatment of brady arrhythmias (slow heart rate). Specifically, bradycardia can be treated by using the INE as a pacing site, as the site of a biological pacemaker that replaces the SA node by accelerating the intrinsic rate of the INE, or as the site of autonomic stimulation to increase the intrinsic pacemaking rate of the INE.

INE as Cell Therapy Site

The INE can also be used as a site for cell therapy delivery for reconstituting a biological pacemaker, because of ease of access via the AV nodal vein, intrinsic pacemaking properties, and high degree of physiological autonomic control as compared with the atrial and ventricular myocardium. To deliver gene therapy or cell therapy to the INE, a catheter, such as the device designs described above, can possess a fluid eluting tip to deliver a saline solution containing the gene or cell therapy. The catheter can further possess a retractable needle, which can extend from the catheter tip to puncture tissue and a sensing electrode to locate the INE. Cell therapy can be delivered through both of the above-described approaches: the endocardial approach or the AV nodal vein approach.

INE as Gene Therapy Site

The INE can also be used as a site for gene therapy. Specifically, the inherent pacemaking properties of the INE can be increased by delivering genes via an electroporating catheter encoding the pacemaker channel isoforms HCN1, HCN2, HCN3, or HCN4 or elements of the autonomic nervous system.

Gene therapy can be delivered in the following manner. A fluid eluting catheter can be placed in the AV nodal vein and the site with the largest slow potential will be located. A second catheter will locate slow potentials on the endocardial surface of the INE. Sub-threshold alternating current (in the range of about 1.0 to about 50.0 microamps, for example) can be passed between the tip of each catheter to minimize the impedance between the two leads and localize the slow pathway. The fluid eluting needle of the venous catheter can extend to puncture the venous wall. Electroporating current can be passed between the two catheters and the saline solution containing the gene therapy will be released simultaneously. Those skilled in the art will recognize that in further embodiments the current of less than about 1 microamp or more than about 50 microamps can be used.

INE for Rate Control

The INE can further be used for rate control during atrial tachyarrhythmias, including atrial flutter and atrial fibrillation, and AVNRT. For example, a stimulation pulse (or a series of pulses) applied to the INE during AVNRT can terminate an arrhythmia without the need for radiofrequency ablation and the potential complications (AV block) that can occur with this procedure.

Stimulation of the autonomic innervation of the INE can be used as an effective treatment for ventricular rate control during atrial fibrillation, such as because of the short refractory period of the INE. Parasympathetic stimulation of the INE can block excitation in the slow pathway, thus, filtering properties of the AV node can be enhanced because excitation of the ventricles will have to travel through the FP, which has a longer refractory period. Pacing of the INE provides conduction via the slow pathway and the lower nodal bundle which has higher safety factor as compared to conduction via the FP and compact AV node. As a result, pacing of the INE can provide safe rate control for atrial arrhythmias without the need of AV nodal ablation in patients with paroxysmal and chronic atrial tachyarrhythmias.

Common forms of AVNRT involve the INE as one pathway of the reentrant arrhythmia, and can be treated by radiofrequency ablation lesions created on or near the INE. In another embodiment, a stimulation pulse, or a series of pulses, applied to the INE during AVNRT can be used to terminate the arrhythmia without the need for radiofrequency ablation and the potential complications, such as, for example, AV nodal block that can occur with this procedure. Each of the tachyarrhythmia therapies can be accomplished with the endocardial or venous approach to the INE using the catheter designs described above.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

APPENDIX A

Nov. 5, 2007

Connexin 43 Expression Delineates Two Discrete Pathways in the Human Atrioventricular Junction Running title: Cx43 in the human AV junction William J. Hucker, Megan L. McCain, Jacob I. Laughner, Paul A. Iaizzo, * Igor R. Efimov Washington University in Saint Louis, Mo. and *University of Minnesota, Minneapolis, Minn.

Address for correspondence: Igor R. Efimov, Department of Biomedical Engineering, Washington University in St. Louis, Mo. 63130. This work was supported by: American Heart Association grant in aid 0750031Z Gap junction expression has been studied in the atrioventricular junction (AVJ) of many species, however their distribution in the human AVJ is unknown. The AVJ expression of the gap junction protein connexin 43 (Cx43) is species dependent; therefore we investigated its distribution in the human AVJ. Methods: Using Masson trichrome histology, we reconstructed the AVJ of 3 normal human hearts and one with dilated cardiomyopathy in 3D. Cx43 was immunolabeled with vimentin and .alpha.-actinin to determine the cellular origin of Cx43, and was quantified in the following structures: interatrial septum (IAS), His bundle, compact node (CN), lower nodal bundle (LNB), leftward and rightward nodal extensions (LE and RE), and inferior, endocardial, and left-sided transitional cells. Results: Histology revealed two nodal extensions in 3/4 hearts. Cx43 was found in the myocytes, but not fibroblasts of the AVJ. LE and CN Cx43 was lower than the IAS (P<0.05) and the RE, LNB, and His all expressed Cx43 similarly, with approximately half of IAS expression (RE: 44.+−0.36%; LNB: 50±26%; His: 48±12%, P=NS compared to IAS). Cx43 levels in transitional cells were similar to the IAS (P=NS). Conclusions: Cx43 was found in myocytes of the human AVJ, and its expression pattern delineates two separate continuous structures: one consists of the LE and CN with little Cx43 and the other consists of the His, LNB and RE expressing approximately half the Cx43 of the IAS. The differential Cx43 expression may provide each structure with unique conduction properties, contributing to arrhythmias arising from the AVJ. Keywords: Atrioventricular node, dual-pathway electrophysiology, connexin43, slow pathway, AVNRT Introduction Detailed investigations of the atrioventricular junction (AVJ) in many animal models have demonstrated the enormous complexity of this structure in terms of cell and tissue morphology, functional characteristics, and protein distribution. While many histological studies have investigated the human AVJ, and clinical electrophysiological studies have provided a substantial amount of information regarding AVJ function in vivo, the number of molecular investigations of the human AVJ is very limited because of the inherent difficulty of procuring human tissue in a timely fashion (Davis et al., 1995). Nevertheless, such studies are vitally necessary to the basic understanding of clinically relevant phenomena, such as atrioventricular nodal reentrant tachycardia (AVNRT) and AV block, and to increase the understanding of variables such as age which are difficult to address in animal models. In addition, interspecies differences in protein expression patterns can limit the extrapolation of animal data to the human (Coppen and Severs, 2002; Coppen et al., 2003). Therefore human molecular studies are crucial because expression patterns in the human AVJ should become the framework in which studies from animal models are interpreted.

Several tissue types are involved in atrial-His conduction, and the term AVJ is used in this study to encompass them all (Billette, 2002). Proximally, the specialized conduction tissue of the AVJ consists of the inferior nodal extensions, which extend from near the coronary sinus (CS) ostium to the node itself (Inoue and Becker, 1998). Previously, these extensions were termed "posterior" rather than "inferior" (Inoue and Becker, 1998; Dobrzynski et al., 2003), however when the heart is oriented anatomically, these extensions actually run inferior to the CN and therefore we use the term "inferior nodal extension" in this study (Cosio et al., 1999). The inferior nodal extensions merge to become the AV node (AVN), which then penetrates the central fibrous body to become the His bundle (Tawara, 1906). Connecting the AVN and nodal extensions to the surrounding atrial tissue are transitional cells that can be divided into three groups based on their location relative to the AVN: endocardial transitional cells contact the AVN on its endocardial aspect, left sided transitional cells approach the AVN from the left side of the interatrial septum (IAS), and inferior transitional cells approach the AVN near the coronary sinus ostium (Anderson and Ho, 2002; Anderson and Ho, 2000).

To accommodate its complex physiological role, the AVJ has developed very heterogeneous gap junction expression, with more types of gap junctional proteins expressed in the AVJ than anywhere else in the heart. Specifically, four cardiac connexins have been described to date (Cx43, Cx40, Cx45, and Cx30.2/31.9), and each of these proteins has been found in animal studies of the AVJ (Boyett et al., 2006). Cx43 and Cx40 are both associated with rapidly conducting cardiac tissues (with Cx40 having a higher conductance than Cx43), and Cx45 and Cx30.2/31.9 are associated with slowly conducting tissues (Boyett et al., 2006). The expression patterns of these connexins in the AVJ are very species dependent: rat hearts do not express Cx43 or 40 in the AVJ, however rabbits express both (Coppen and Severs, 2002; Dobrzynski et al., 2003). Only one study has documented the expression of connexins in the human AVJ to our knowledge (Davis et al., 1995), where they found that Cx43, Cx40, and Cx45 were all present, yet this study did not survey where in the AVJ each connexin was expressed.

Traditionally, connexins have been assumed to form gap junctions between two adjacent myocytes. However, recent publications also suggest that functional gap junctions are formed between myocytes and fibroblasts (Camelliti et al., 2005), possibly via Cx43 coupling (Goldsmith et al., 2004). In this study, we investigated Cx43 expression throughout the various tissues of the AVJ, as well as whether Cx43 forms gap junctions between myocytes and fibroblasts. We correlated Cx43 immunofluorescence with 3D reconstructions of the AVJ constructed from Masson trichrome histology, showing that Cx43 expression pattern delineates domains of the AVJ (not apparent with histology) that may have functional consequences.

Methods

The use of human hearts for research was approved by the Institutional Review Boards at Washington University and the University of Minnesota. Three specimens were provided by the Upper Midwest Organ Procurement Organization (LifeSource, St. Paul, Minn.; they also provided pre-approval for this protocol); these hearts were deemed non-viable for transplantation. An additional specimen was a transplant recipient's explanted heart with idiopathic dilated cardiomyopathy (DCM). The clinical data that is known regarding each specimen is shown in Table 1, of FIG. 24. These specimens were placed in frozen tissue embedding media (Histo Prep.™, Fisher Scientific, Fair Lawn, N.J.) and stored in a $-80°$ C. freezer at the University of Minnesota, before being shipped on dry ice to Washington University. Subsequently, they were thawed at $4°$ C. before dissection. The triangle of Koch was exposed, and an approximately $4.\text{times}.4\ \text{cm}^2$ area of tissue at the apex of the triangle of Koch was dissected (FIG. 1A) and re-frozen at $-80°$ C. The tissue blocks were cryosectioned at 16 µm, mounted on Superfrost Plus glass slides (Fisher Scientific), and stored at $-80°$ C. until use. The location of each tissue section was documented throughout the sectioning process.

3D Reconstruction

To create a 3D reconstruction of the AV junction, tissue sections approximately 0.5-1.0 mm apart (FIG. 15B) were stained with Masson trichrome. Histology sections were photographed with a 2.times. lens and a mosaic image of the tissue section was created. The image of each section was imported into Rhinoceros NURBS modeling for Windows version 3.0 (Robert McNeel & Associates) and outlined to separate areas of: fat as well as any imbedded strands of transitional cells, IAS/transitional cells, ventricular septum, connective tissue (central fibrous body, mitral and tricuspid valves), conduction system (His bundle, compact AV node, lower nodal bundle, rightward and leftward inferior nodal extensions), and major arteries and veins (FIG. 15C). Transitional cells were incorporated into the areas of the IAS or the fatty tissue surrounding the conduction system because the transitional cell boundary was difficult to define and quite irregular, which made 3D reconstruction of transitional cells confusing and unclear. However in FIG. 15C, arrows point to transitional cells that lie within the fatty tissue, and arrowheads point to transitional cells from the left atrium. The set of derived outlines from each section was rotated and aligned to those of the previous section. The correct 3D placement of each section was determined by using distances recorded during tissue cryo sectioning. FIG. 15D shows the resultant correctly aligned and positioned outlines for the conduction system in the explanted heart from the patient with DCM. For each tissue type, the set of outlines was lofted to create a mesh approximating the 3D volume (FIG. 15E), which was then rendered to create a solid 3D volume (FIG. 15F).

Immunohistochemistry

For immunohistochemistry, tissue sections were first fixed, permeabilized, and blocked by immersion in 3.7% formaldehyde for 5 minutes, 0.15% Triton for 15 minutes, and 10% normal horse serum for 60 minutes. Using immunohistochemistry, we visualized three different proteins: the gap junctional protein Cx43, the myocyte marker α-actinin which is expressed in the sarcomeres of myocytes, and the intermediate filament protein vimentin, which is expressed in the cytoskeletal intermediate filaments of fibroblasts and endothelial cells (Camelliti et al., 2005). In cardiac tissue, endothelial cells are present in blood vessels, whereas fibroblasts are present throughout the myocardial tissue. Therefore, fibroblasts can be differentiated from endothelial cells based on location in the tissue and we used this marker to visualize fibroblasts in the myocardium. The following primary antibodies were applied overnight at 4.degree. C.: rabbit anti-Cx43 (Sigma, 1:1000), mouse anti-.alpha.-actinin (sarcomere specific, Sigma, 1:1600), and guinea pig anti-vimentin (Progen, 1:800). The following secondary antibodies were applied for 2 hours at room temperature: Alexa Fluor 555 goat anti-rabbit IgG (Molecular Probes, 1:800), Alexa Fluor 488 goat anti-mouse IgG.sub.1 (Molecular Probes, 1:800), and Alexa Fluor 647 goat anti-guinea pig IgG (Molecular Probes, 1:800). Immunofluorescent studies in human cardiac tissue can be quite difficult due to autofluorescence (Billinton and Knight, 2001), therefore sections were immersed in a 1% Sudan Black (Sigma) solution for 10 minutes (Schnell et al., 1999) to reduce autofluorescence originating from lipofuscin particles found in human tissue. Tissue sections were subsequently mounted with ProLong Gold antifade reagent with DAPI (Invitrogen).

Connexin Quantification

Confocal immunohistochemical images were collected using a 40× lens and individual images were pieced together to create a mosaic image at three different planes within the AVJ. The first plane was a section through the inferior nodal extensions, the second plane was through the compact AV node (CN), and the third plane was through the His bundle. In the first plane, Cx43 was quantified in the leftward inferior nodal extension, rightward extension, inferior transitional cells, and the IAS. In the second plane, Cx43 was quantified in the CN, lower nodal bundle (LNB), endocardial transitional cells, left atrial transitional cells and the IAS. Finally in the third plane, Cx43 was quantified in the His bundle and the interatrial septum (IAS). Connexin densities within the various regions of the tissue were determined using a custom program (MATLAB, Mathworks, Natick, Mass.). A full description of the algorithm has been published previously (Hucker et al., 2007a) and is provided in the online data supplement. Briefly, the mosaic image of the area of interest was thresholded twice to produce two black and white images of the Cx43 channel. The first threshold selected positive Cx43 staining in the image. The second threshold was much lower than the first and selected any tissue in the image. The area of each was corrected, and the Cx43 area was divided by the tissue area to give a percentage of the tissue area that corresponded to Cx43 staining (see online data supplement).

Colocalization

Colocalization plots were used to determine which cell types expressed Cx43. In a three channel, three dimensional confocal Z-stack, each voxel has three intensity values, one each for red, green, and blue staining A colocalization plot, generated with Volocity (Improvision, Inc., Lexington, Mass.), displays two of these intensity values as a function of each other. By definition, two proteins are highly colocalized in a particular volume when fluorescence intensities corresponding to these two proteins are high in the voxel corresponding to this volume. Therefore, if two proteins are colocalized in many voxels, the colocalization plot will contain a significant diagonal distribution. Voxels with the highest degree of colocalization will be displayed in the upper-right quadrant. In contrast, if the two proteins are not colocalized, the colocalization plot shows voxel values near each axis, with no diagonal elements present.

Statistics

Cx43 quantification data are represented as mean±standard deviation. Cx43 levels were compared using the non-parametric Kruskal Wallis test (MATLAB). A value of $p<0.05$ was considered statistically significant.

Results

Cx43 Expression in the Conduction System

Figure 16:
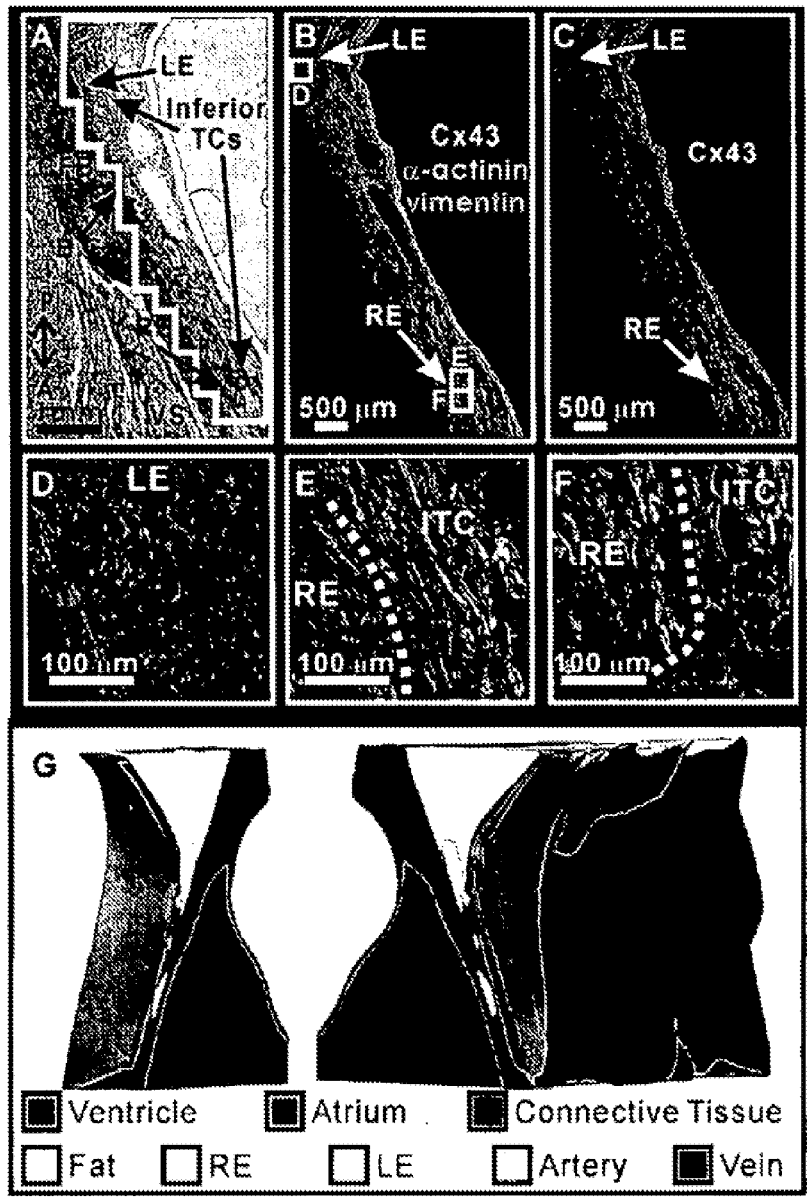
FIG. 16 illustrates Cx43 density in the nodal extension.

For one representative AVJ preparation, Masson trichrome histology, Cx43 immunofluorescence, and the 3D reconstruction of the preparation is shown in FIGS. 16-18. Inferiorly, the AVN begins as the inferior nodal extensions, which vary both in length and number (Inoue and Becker, 1998). In three of the four hearts in this study, there were two inferior nodal extensions, while the other had only one. The preparation shown in FIGS. 16-18 possessed both a leftward and rightward extension: the leftward extension begins near the left side of the IAS, whereas the rightward extension lies adjacent to the septal leaflet of the tricuspid valve (FIG. 16A). While the rightward extension expressed Cx43 (FIGS. 16E and 16F), there was virtually no Cx43 present in the leftward extension (FIG. 16D). In this preparation, the rightward extension was located in close proximity to layers of inferior transitional cells, which also expressed Cx43 (FIGS. 16E and 16F). Transitional cells were found closely related to the rightward extension in 3 of 4 preparations. Additionally, large veins were observed in close proximity to the rightward extension in each preparation, as seen in FIGS. 16A-C. Between the leftward extension and the rightward extension, there was a variable amount of Cx43 negative tissue which was continuous with the compact AVN superiorly (FIG. 16C). The amount of this tissue varied between preparations. Throughout FIG. 16 it is clear that fibroblasts are interspersed between the myocytes of the rightward and leftward extensions, as shown with vimentin staining (blue). The 3D reconstruction of this preparation is shown in FIG. 16G, split open at the plane shown in FIGS. 16A-C to display the rightward and leftward extensions within the tissue.

FIG. 17 illustrates the Masson trichrome, Cx43 expression, and 3D reconstruction of the AVN in this preparation. The AVN is bordered by the central fibrous body (CFB), a layer of fibrofatty tissue separating the AVN from atrial tissue, and by thin layers of endocardial transitional cells as seen in FIG. 17A. On the posterior aspect of the AVN, transitional cells which connect the left side of the IAS to the AVN make contact with AVN tissue. Many strands of transitional cells also lie within the fibrofatty tissue layer, however these strands of tissue were not outlined separately in the reconstruction.

The AVN can be divided into the compact node (CN) and the lower nodal bundle (LNB) based on functional and morphological characteristics (Anderson et al., 1974; Billette, 2002). The CN is composed of small densely packed irregularly shaped cells, whereas the LNB cells are larger and oriented parallel to each other. We observed a consistent heterogeneity in Cx43 expression between these two structures. The LNB, which occupies the anterior portion of the AVN, closest to the ventricle, expressed more Cx43 than the posterior CN region, closest to the atrium (FIGS. 17B, C, and G). Inferiorly, the CN was continuous with the leftward extension, and the LNB was continuous with the rightward extension. Therefore the CN and leftward extension were outlined as one continuous structure in the reconstruction. Likewise, the rightward extension and LNB were reconstructed as a single volume (FIG. 17H). Both sets of transitional cells that are visible in this section, the left sided and the endocardial transitional cells, expressed high levels of Cx43, similar to the IAS (FIGS. 17D and E). As can be seen in FIG. 17, an extensive network of fibroblasts was present around the myocytes of the conduction system in the entire AVN region (FIGS. 17B, F, and G).

FIG. 18 displays the His bundle of this preparation. The His bundle is completely surrounded by the fibrous tissue of the central fibrous body (CFB), as seen in both the histology and the 3D reconstruction (FIGS. 18A and 18E). The proximal end of the His bundle was defined as the point where the AVN was completely surrounded by the CFB, which was the transition point suggested by Tawara between the AVN and the His bundle (Tawara, 1906). The His bundle was reconstructed from this point to the point where it joined the ventricular septum.

Cx43 was heterogeneously expressed throughout the His bundle, as seen in FIGS. 18B and 18C. In this example, a higher level of Cx43 expression is seen on the endocardial and ventricular aspects of the His bundle. However this pattern was not consistent; in other preparations Cx43 was highly expressed on the atrial border of the His bundle. While Tawara's transition point between the His bundle and the AVN is convenient morphologically, we did not observe an abrupt change in Cx43 expression at the beginning of the His bundle as defined by Tawara. Instead Cx43 expression gradually changed from the CN/LNB pattern seen in the AVN to the pattern shown in the His bundle. As can be seen in FIGS. 18B and 18D, a large number of fibroblasts are also present in the His bundle surrounding most of the His bundle myocytes.

Even though an extensive network of fibroblasts was present throughout the AVJ, as seen in FIGS. 16-18, we found that the overwhelming majority of Cx43 was solely expressed within the myocytes, with exceedingly few examples of Cx43 within fibroblasts or between myocytes and fibroblasts. FIG. 19 displays maximum projection images of two representative, high resolution 3D confocal image stacks where α-actinin, vimentin, and Cx43 were labeled. Using the method of colocalization plots, we determined the cellular origin of Cx43 in each voxel. In panels A-C, data recorded from the LNB are displayed. The maximum projection image illustrates that fibroblasts surround the myocytes, however Cx43 is expressed solely within and between the myocytes. In panel B, a colocalization plot illustrates the red and green intensity values of each voxel within the volume imaged. The voxels which had high green intensities (i.e. specific Cx43 staining) were spread across the values of the α-actinin axis, indicating that Cx43 staining was present in voxels which also expressed α-actinin. In panel C, a colocalization plot of the blue and green intensity values from the same volume is displayed. In this plot, the voxels of specific Cx43 staining are clustered along the Cx43 axis, indicating that specific staining of Cx43 only occurred in voxels with no blue intensity. In fact, of the 14,490 voxels in this particular volume that were in the upper half of Cx43 intensity, only 1 voxel was also in the upper half of vimentin intensity. FIGS. 19D-F illustrates the same pattern of Cx43 expression in the CN. In the CN, there is much less Cx43 than in the LNB (FIG. 17), however the colocalization plots in panel E and F indicate that whatever Cx43 is expressed in the CN is within or between myocytes, with very few voxels of specific Cx43 staining having any blue intensity. In this volume, 34 of the 953 voxels in the upper half of Cx43 staining were also in the upper half of vimentin staining, however these voxels were not clustered together in one location. Instead, they appeared as one or two voxels that were independent of each other. Thus, we conclude that there very little evidence for gap junction formation between myocytes and fibroblasts in the human AVJ.

Cx43 Quantification

Figure 20:
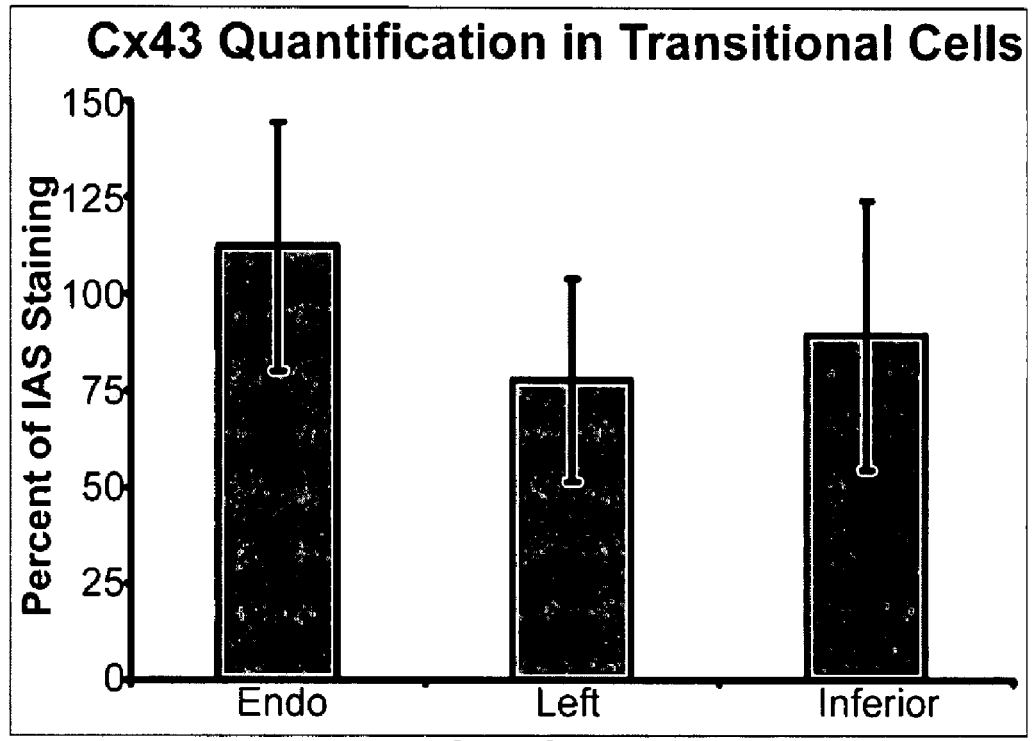
FIG. 20 illustrates Cx43 density in transitional cells in the AVJ.

Cx43 was quantified throughout the various tissue types in the AVJ. For comparison, Cx43 was also quantified in the IAS in each tissue section. Cx43 expression was relatively constant between the three different groups of transitional cells and the IAS, as shown in FIG. 20. When expressed as a percentage of IAS Cx43, Cx43 in the endocardial transitional cells was 112±32%, 78±26% in the left sided transitional cells, and 89±35% in the inferior transitional cells (P=NS for each).

Figure 21:
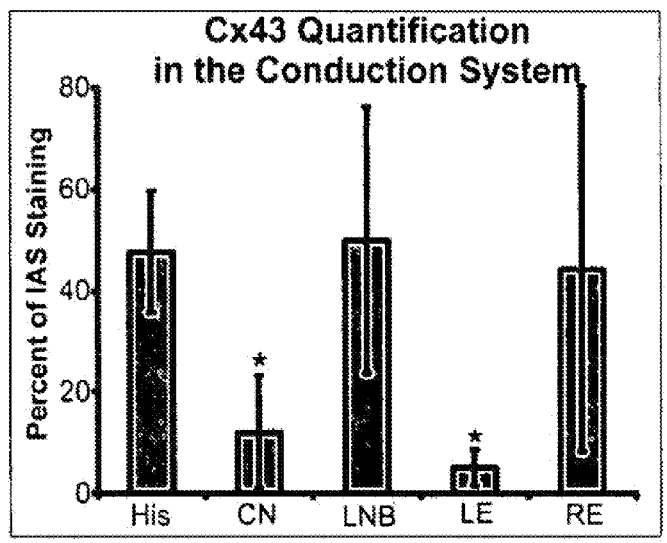
FIG. 21 illustrates Cx43 density in the conduction system of the AVJ.

When Cx43 was quantified in the conduction system of each preparation, a distinct pattern emerged as shown in the bar graph in FIG. 21. The rightward extension, LNB, and His bundle all expressed Cx43 similarly to each other (ratio to the IAS was 44±36%, 50±26%, and 48±12% respectively). While the average Cx43 expression in each of these structures was not statistically different from the IAS due to the small number of hearts in this study, it is clear that the Cx43 expression was consistent between them. However Cx43 expression in the leftward extension and the CN were both statistically lower than in the IAS (5±4% and 12±11% of the IAS signal respectively, P<0.05 for each). Cx43 expression was also statistically lower in the leftward extension and the CN than in the LNB (P=0.03 and P=0.02, respectively).

Conduction System Reconstruction

The 3D reconstructions of the conduction system from each heart, consisting of the leftward and rightward extensions, CN, LNB, and His bundle is shown in two views in FIG. 22. Each panel shows the reconstruction of the conduction system of one heart. The left view of each panel demonstrates the orientation of the conduction system within the triangle of Koch, blood vessels located in close proximity to the conduction system, and the CFB, which encases the His bundle. The right view shows the conduction system by itself, and the three planes where Cx43 expression was quantified. The His bundle of each preparation is shown in green. The LNB and rightward extension are depicted as a continuous structure in yellow. The leftward extension and CN are shown as a continuous structure in cyan. Finally layers of inferior transitional cells which were closely related to the rightward extension are shown in orange. These areas of close apposition between transitional cells and the rightward extension may be the interface between the atrial myocardium and the nodal extension. In two preparations (FIGS. 22A and B), the rightward extension was longer than the leftward extension. As seen in FIG. 22C, one preparation had a rightward, but no leftward extension, and finally in the heart with DCM (panel D) the leftward extension was actually slightly longer than the rightward extension.

In the DCM heart (FIG. 22D), the IAS was much thicker than in the other three preparations, and in this heart the leftward extension protrudes prominently towards the left atrial side of the IAS (in the dorsal-ventral direction). Therefore, an additional view of the conduction system, which is rotated 90° from the endocardial view shown in panels A-C, is shown in panel D. The conduction system in the DCM heart was thicker than those of the normal hearts, as can be seen in FIG. 22D. Animations of the reconstruction of the DCM heart and the normal heart in panel A are provided in the online data supplement.

Discussion

In this study, we have reconstructed the 3D anatomy of the conduction system in the human AVJ and mapped the distribution and cellular origin of Cx43. Our results indicate that Cx43 is distributed heterogeneously in the myocytes of the region: the rightward extension, LNB, and His bundle express similar levels of Cx43 (approximately half the level of IAS expression), while the leftward extension and the CN express very little Cx43 as compared to the IAS.

Inoue and Becker described a series of 21 hearts where they found that 7/21 (33%) had only a rightward but no leftward extension, 13/21 (62%) had a rightward extension that was longer than the left, and 1/21 (5%) that had only a leftward extension (Inoue and Becker, 1998). Our sample of hearts closely mimics those described by Inoue and Becker: 2/4 (50%) had a longer rightward extension than leftward, and 1/4 (25%) had only a rightward extension. Interestingly, in the DCM heart of our study the leftward extension was actually longer than the rightward extension, which is a variant that Inoue and Becker did not observe. Whether this variation is simply rare and did not surface in their investigations, or whether it is due to the pathologic state of this sample can not be determined from our study. It is certainly possible that the long leftward extension is related to the DCM because the overall morphology of the conduction system was different in this heart (FIG. 15C), and it was larger than the other hearts in this study (FIG. 22D). The thickness of the IAS was also much greater in this heart than in the other hearts (data supplement movie 2), and therefore the leftward extension may have elongated preferentially in this heart as the myocardium remodeled because it was oriented in the dorsal-ventral direction. We also found that the Cx43 expression in this heart was higher than the normal hearts (FIGS. 20 and 21), however a previous study demonstrated that left ventricular Cx43 expression is reduced in patients with DCM (Dupont et al., 2001). Therefore future studies will be necessary to determine the effect of various cardiomyopathies on the AVJ.

In the study of Inoue and Becker (1998) which was entirely based upon histological investigations, no mention of the LNB was made. In part, this may be due to the fact that the LNB of the human is difficult to recognize with histology alone. In this study, we found that with the additional use of the Cx43 marker, we could consistently visualize the LNB, which indicates that morphologically similar cells and structures can possess very different molecular characteristics. Future studies will be necessary to determine if other connexin isoforms delineate similar domains throughout the human AVJ.

The rabbit AVJ is often used as an experimental model of the human AVJ. In the rabbit, there is only one nodal extension which lies below the right atrial endocardium in the myocardial isthmus between the coronary sinus and tricuspid valve, very similar to the position of the human rightward extension. In this study, Cx43 quantification revealed two axes of Cx43 expression in the human AVJ: the rightward extension, LNB, and the His bundle all express Cx43 similarly to each other and at higher levels than the CN and leftward extension. A previous study reported that the rabbit also has two domains of Cx43 expression. Ko et al found that the His bundle, lower nodal cells, and the nodal extension all express Cx43 similarly and that the CN does not express detectable Cx43 (Ko et al., 2004). Therefore it is consistent between the human and the rabbit that the rightward extension/LNB is connected to the His bundle differently than the leftward extension/CN. The similarity between the data in this study and rabbit investigations provides further evidence that the rabbit is an appropriate model of the human cardiac conduction system (Rothenberg and Efimov, 2006).

Using the method of colocalization plots, we have concluded that the interaction between fibroblasts and myocytes via Cx43 is minimal if any in the human AVJ (FIG. 19). The colocalization technique is useful to tease out the location of immunofluorescent signals in 3D space. It is also quantitative: it displays the values of every voxel within a stack of images, which removes any selection bias from the results. However this technique assumes that if fibroblasts express Cx43, the signal would be colocalized with vimentin. This assumption may or may not be correct because vimentin is a cytosolic protein and Cx43, if expressed and functional, would be membrane bound. However at the optical resolution used in this study, the pixel resolution of our confocal images is 240 nm in X and Y (125×125 µm field of view with 512×512 pixels) and ~500 nm in Z which is quite large with respect to the separation of proteins in a cell. It seems reasonable that vimentin fibers would be expressed within 240 nm of the cell membrane, therefore we feel that our assumption is valid. Also, the same restrictions on the physical overlap of α-actinin and Cx43 would apply because sarcomere specific α-actinin would be expressed in the cytosol of myocytes, yet the colocalization plot indicates that there is colocalization between α-actinin and Cx43.

Functional Implications

Dual pathway electrophysiology is one of the pathological hallmarks of the human AVJ, providing the substrate for reentrant arrhythmias such as AV nodal reentrant tachycardia (AVNRT) (Moe et al., 1956). Typically the AVJ is described as having two functional pathways, a slow and a fast pathway, which give rise to AVNRT. Anatomically, the substrate for the slow pathway involves the isthmus of myocardium between the coronary sinus and the tricuspid valve (Nikolski et al., 2003) which is ablated to treat AVNRT, and transitional cells act as the fast pathway. There is evidence that the rightward extension is the substrate of the slow pathway (Inoue et al., 1999; Medkour et al., 1998), however it is debated whether the rightward extension, the inferior transitional cells which overlay this extension, or a combination of both is the true substrate of the slow pathway (McGuire, 2000). If the rightward extension is indeed a substrate of the slow pathway, it is intriguing that our results indicate that the rightward extension contains a relatively large amount of Cx43 because Cx43 expression would imply fast conduction. However conduction velocity is not solely dependent upon Cx43 expression; Cx40, Cx45, possibly Cx30.2/31.9 (Kreuzberg et al., 2006), as well as ion channel expression will certainly affect conduction velocity in the nodal extensions. In reality, it may not be conduction time within the inferior nodal extension that is responsible for the "slow" nature of the slow pathway, but it may be the interface between the inferior transitional cells and the inferior nodal extension that is responsible for slow conduction (Hucker et al., 2007b; Nikolski et al., 2003). However, future studies correlating functional properties of the nodal extensions with the distribution of Cx40, Cx45, Cx30.2/31.9 as well as ion channel distributions will be necessary to fully understand the role of the nodal extensions in AVNRT.

We found that the probable substrate of the fast pathway, the transitional cell layers around the CN, expressed Cx43 at similar levels to the atrial septum which would functionally support fast conduction within these cell layers. Both structurally and functionally, these cells are intermediate between the atrial myocardium and the AVN in terms of action potential characteristics and cell morphology (Anderson and Ho, 2002; Billette, 1987). However in terms of Cx43 expression, FIG. 17C shows that instead of a smooth transition in Cx43 at the interface of the transitional cells and the CN, there is a dramatic decrease in Cx43 expression from the transitional cells to the CN, which may slow action potential propagation into the CN (Shaw and Rudy, 1997).

The role of the leftward extension/compact nodal structure is less clear. Because it expresses little Cx43, this structure would presumably conduct slowly and may provide a slowly conducting pathway in cases of AVNRT where more than one slow pathway is observed, or in intranodal reentry. Consistent with this hypothesis is the correlation between the fact that AVNRT involving multiple pathways is less common than AVNRT involving one slow pathway, and the leftward extension is inconsistently expressed in humans (Inoue and Becker, 1998). The leftward extension could also provide a slowly conducting pathway between the left atrial side of the LAS and the nodal tissue (Katritsis and Becker, 2007). Finally, inferior transitional cells come into close proximity to the leftward extension in some cases (FIGS. 18A-C) and therefore a reentry circuit may possibly be sustained between the two nodal extensions and the inferior transitional cells.

The continuous expression of Cx43 from the rightward INE to the LNB and the His bundle implies that these structures form one continuous structure and that the rightward extension is connected to the His bundle differently than the leftward extension. In the rabbit, functional studies in our lab and others have indicated that excitation spreading from the inferior nodal extension excites the His bundle differently than excitation spreading from the fast pathway (Hucker et al., 2007b; Zhang et al., 2001), and specifically that the AV delay can be avoided by pacing near the inferior nodal extension (Hucker et al., 2007b). Our data in this study suggest that the same may be true in the human with excitation in the rightward extension spreading via the LNB to a specific Cx43 positive domain of the His bundle, bypassing the compact AV node.

The possibility of unique coupling between the rightward extension and the His bundle opens the possibility of exploiting this connection to achieve His bundle excitation without engaging the compact AV node. Recent pacing strategies have explored alternative pacing sites, such as direct His bundle pacing, to achieve synchronized ventricular contraction (Laske et al., 2006; Deshmukh and Romanyshyn, 2004; Zanon et al., 2006). Attempting to pace the rightward extension rather than the His bundle itself would expand the area at the base of the right atrium where a pacing lead could be implanted and potentially lower pacing thresholds because the rightward extension is not encased in fibrous tissue like the His bundle.

Our 3D reconstruction of the human AVJ indicated that the tissue surrounding the conduction system is richly vascularized. The veins surrounding the AVJ are large, with diameters ranging from 0.29-0.56 mm in the 4 AVJs we reconstructed. Because the coronary sinus is located very close to the AVJ, the veins shown in the 3D reconstructions of FIG. 8 either join the coronary sinus very near its os, or drain into the right atrium directly. While CS os access can be challenging in some patients (Hill et al., 2006), it may soon be possible to navigate these veins with catheters for ablations, pacing, or localized pharmacologic delivery (e.g. to achieve AVN modulation during atrial fibrillation) without the tissue damage induced by an active lead screwed into the myocardium (Sigg et al., 2006).

CONCLUSIONS

Our study presents for the first time the mapping of Cx43 in the human AVJ. We have found that the conduction system in the human AVJ expresses two domains with respect to Cx43 density: the rightward extension, LNB, and His bundle all express Cx43 similarly to each other, while the leftward extension and the CN possess very little Cx43. These two separate domains may therefore possess unique conduction properties that contribute to heterogeneous conduction and supraventricular arrhythmias arising from the AVJ.

Limitations

Our study was limited to a single connexin isoform, Cx43. However, other isoforms are known to be expressed in the AVJ of mammalian species, including Cx45, Cx40, and Cx31.9/Cx30.2. Unfortunately, we were unable to obtain antibodies to these connexins which would provide quantifiable signals in the human AVJ. Additionally, our study was based on immunohistochemistry, and therefore the detection of Cx43 was limited by the resolution of this technique. It is certainly possible that gap junctions composed of Cx43 were small enough to escape detection with immunofluorescence.

Our study was conducted in human hearts which were not previously characterized in the electrophysiology lab.

REFERENCE LIST

Anderson R H, Ho S Y. 2000. The Atrial Connections of the Specialized Axis Responsible for AV Conduction. In: Mazgalev T N, Tchou P J, editors. Atrial-AV Nodal Electrophysiology: A View from the Millenium. Armonk, N.Y.: Futura Publishing Company. p 3-24.

Anderson R H, Ho S Y. 2002. The morphology of the specialized atrioventricular junctional area: the evolution of understanding. Pacing Clin Electrophysiol 25:957-966.

ANDERSON R H, Durrer D, JANSE M J, VAN CAPELLE F J L, BILLETE JACQ, Becker A E, DURRER DIRK. 1974. A Combined Morphological and Electrophysiological Study of the Atrioventricular Node of the Rabbit Heart. Circ Res 35:909-922.

Billette J. 1987. Atrioventricular nodal activation during periodic premature stimulation of the atrium. Am J Physiol 252:H163-H177.

Billette J. 2002. What is the atrioventricular node? Some clues in sorting out its structure-function relationship. J Cardiovasc Electrophysiol 13:515-518.

Billinton N, Knight A W. 2001. Seeing the Wood through the Trees: A Review of Techniques for Distinguishing Green Fluorescent Protein from Endogenous Autofluorescence. Analytical Biochemistry 291:175-197.

Boyett M R, Inada S, Yoo S, Li J, Liu J, Tellez J, Greener I D, Honjo H, Billeter R, Lei M, Zhang H, Efimov I R, Dobrzynski H. 2006. Connexins in the sinoatrial and atrioventricular nodes. Adv Cardiol 42:175-197.

Camelliti P, Borg T K, Kohl P. 2005. Structural and functional characterisation of cardiac fibroblasts. Cardiovascular Research 65:40-51.

Coppen S R, Kaba R A, Halliday D, Dupont E, Skepper J N, Elneil S, Severs N J. 2003. Comparison of connexin expression patterns in the developing mouse heart and human foetal heart. Mol Cell Biochem 242:121-127.

Coppen S R, Severs N J. 2002. Diversity of connexin expression patterns in the atrioventricular node: vestigial consequence or functional specialization? J Cardiovasc Electrophysiol 13:625-626.

Cosio F G, Anderson R H, Kuck K H, Becker A, Borggrefe M, Campbell R W, Gaita F, Guiraudon G M, Haissaguerre M, Rufilanchas J J, Thiene G, Wellens H J, Langberg J, Benditt D G, Bharati S, Klein G, Marchlinski F, Saksena S. 1999. Living anatomy of the atrioventricular junctions. A guide to electrophysiologic mapping. A Consensus Statement from the Cardiac Nomenclature Study Group, Working Group of Arrhythmias, European Society of Cardiology, and the Task Force on Cardiac Nomenclature from NASPE. Circulation 100:e31-e37.

Davis L M, Rodefeld M E, Green K, Beyer E C, Saffitz J E. 1995. Gap junction protein phenotypes of the human heart and conduction system. J Cardiovasc Electrophysiol 6:813-822.

Deshmukh P M, Romanyshyn M. 2004. Direct his-bundle pacing: Present and future. Pace-Pacing and Clinical Electrophysiology 27:862-870.

Dobrzynski H, Nikolski V P, Sambelashvili A T, Greener I D, Yamamoto M, Boyett M R, Efimov I R. 2003. Site of origin and molecular substrate of atrioventricular junctional rhythm in the rabbit heart. Circ Res 93:1102-1110.

Dupont E, Matsushita T, Kaba R A, Vozzi C, Coppen S R, Khan N, Kaprielian R, Yacoub M H, Severs N J. 2001. Altered Connexin Expression in Human Congestive Heart Failure. Journal of Molecular and Cellular Cardiology 33:359-371.

Goldsmith E C, Hoffman A, Morales M O, Potts J D, Price R L, McFadden A, Rice M, Borg T K. 2004. Organization of fibroblasts in the heart. Dev Dyn 230:787-794.

Hill A J, Ahlberg S E, Wilkoff B L, Iaizzo P A. 2006. Dynamic obstruction to coronary sinus access: The Thebesian valve. Heart Rhythm 3:1240-1241.

Hucker W J, Nikolski V P, Efimov I R. 2007a. Autonomic control and innervation of the atrioventricular junctional pacemaker. Heart Rhythm 4:1326-1335.

Hucker W J, Sharma V, Nikolski V P, Efimov I R. 2007b. Atrio-Ventricular Conduction with and without AV Nodal Delay: Two Pathways to the Bundle of His in the Rabbit Heart. Am J Physiol Heart Circ Physiol 00115.

Inoue S, Becker A E. 1998. Posterior extensions of the human compact atrioventricular node: a neglected anatomic feature of potential clinical significance. Circulation 97:188-193.

Inoue S, Becker A E, Riccardi R, Gaita F. 1999. Interruption of the inferior extension of the compact atrioventricular node underlies successful radio frequency ablation of atrioventricular nodal reentrant tachycardia. J Intery Card Electrophysiol 3:273-277.

Katritsis D G, Becker A. 2007. The atrioventricular nodal reentrant tachycardia circuit: A proposal. Heart Rhythm 4:1354-1360.

Ko Y S, Yeh H I, Ko Y L, Hsu Y C, Chen C F, Wu S, Lee Y S, Severs N J. 2004. Three-dimensional reconstruction of the rabbit atrioventricular conduction axis by combining histological, desmin, and connexin mapping data. Circulation 109:1172-1179.

Kreuzberg M M, Schrickel J W, Ghanem A, Kim J S, Degen J, Janssen-Bienhold U, Lewalter T, Tiemann K, Willecke K. 2006. Connexin30.2 containing gap junction channels decelerate impulse propagation through the atrioventricular node. Proc Natl Acad Sci USA 103 :5959-5964.

Laske T G, Skadsberg N D, Hill A J, Klein G J, Iaizzo P A. 2006. Excitation of the intrinsic conduction system through His and interventricular septal pacing. Pace-Pacing and Clinical Electrophysiology 29:397-405.

McGuire M. 2000. What is the Slow AV Nodal Pathway? In: Mazgalev T N, Tchou P J, editors. Atrial-AV Nodal Electrophysiology: A View from the Millenium. Armonk: Futura. p 183-197.

Medkour D, Becker A E, Khalife K, Billette J. 1998. Anatomic and Functional Characteristics of a Slow Posterior AV Nodal Pathway: Role in Dual-Pathway Physiology and Reentry. Circulation 98:164-174.

MOE G K, PRESTON J B, BURLINGTON H.1956. Physiologic evidence for a dual A-V transmission system. Circ Res 4:357-375.

Nikolski V P, Jones S A, Lancaster M K, Boyett M R, Efimov I R. 2003. Cx43 and the Dual-Pathway Electrophysiology of the AV Node and AV Nodal Reentry. Circ Res 92:469-475.

Rothenberg F, Efimov I R. 2006. Three-dimensional anatomy of the conduction system of the early embryonic rabbit heart. Anat Rec A Discov Mol Cell Evol Biol 288:3-7.

Schnell S A, Staines W A, Wessendorf M W. 1999. Reduction of Lipofuscin-like Autofluorescence in Fluorescently Labeled Tissue. J Histochem Cytochem 47:719-730.

Shaw R M, Rudy Y. 1997. Ionic Mechanisms of Propagation in Cardiac Tissue: Roles of the Sodium and L-type Calcium Currents During Reduced Excitability and Decreased Gap Junction Coupling. Circ Res 81:727-741.

Sigg D C, Hiniduma-Lokuge P, Coles J A, Jr., Falkner P, Rose R, Urban J F, Ujhelyi M R. 2006. Focal Pharmacological Modulation of Atrioventricular Nodal Conduction via Implantable Catheter: A Novel Therapy for Atrial Fibrillation? Circulation 113:2383-2390.

Tawara S. 1906. Das Reizleitungssystem des Saugetierherzens: Eine Anatomische-Histologische Studie Uber Das Atrioventrikularbundel Und Die Purkinjeschen Faden. Jena: Verlag von Gustav Fischer.

Zanon F, Baracca E, Aggio S, Pastore G, Boaretto G, Cardano P, Marotta T, Rigatelli G, Galasso M, Carraro M, Zonzin P. 2006. A feasible approach for direct His-bundle pacing using a new steerable catheter to facilitate precise lead placement. Journal of Cardiovascular Electrophysiology 17:29-33.

Zhang Y, Bharati S, Mowrey K A, Zhuang S, Tchou P J, Mazgalev T N. 2001. His electrogram alternans reveal dual-wavefront inputs into and longitudinal dissociation within the bundle of His. Circulation 104:832-838.

Table and Figure Legends

Table 1: Patient Characteristics for Each Sample Used in this Study

FIG. 15: Dissection of human AV junction and creation of 3D reconstruction. A: Dissected AV junctional preparation with anatomical landmarks labeled. B: High resolution image of the boxed area in A, with locations of sections stained with Masson trichrome marked. Also the triangle of Koch is outlined, which is bounded by the tendon of Todaro (TT), the coronary sinus (CS) and the septal leaflet of the tricuspid valve (TV). C: Masson trichrome staining of section marked by a red line in B with different tissue areas outlined for 3D reconstruction. D: Outlines of the conduction system of all sections aligned in three dimensions. Red outline corresponds to the AV node outlined in C. E: Outlines of the conduction system lofted to create a 3D mesh. F: 3D mesh in E rendered to approximate the 3D volume. AVN: AV node; CFB: central fibrous body; FO, fossa ovalis. IAS: interatrial septum; LE: leftward extension; RE: rightward extension; VS: ventricular septum; S,I,P,A: Superior, inferior, posterior, anterior orientation.

FIG. 16: Cx43 density in the nodal extensions. A: Masson trichrome stain of the nodal extensions. Outlined area surrounding the nodal extensions corresponds to immunohistochemistry shown in panels B and C. B: Immunohistochemistry of the nodal extensions showing $\alpha$-actinin in red, vimentin in blue, and Cx43 in green. C: Cx43 expression in the nodal extensions. D-F: Higher magnification of Cx43, vimentin, and $\alpha$-actinin expression in leftward extension (D), the rightward extension, and the inferior transitional cells (E and F). G: 3D reconstruction of the AVJ split open at the plane of section shown in panels A-C. CFB: central fibrous body; IAS: interatrial septum; LE: leftward extension; RE: rightward extension; VS: ventricular septum; P,A: Posterior-anterior orientation.

FIG. 17: Cx43 density in the AV node. A: Masson trichrome stain of the AVN. Outlined area surrounding the AVN corresponds to immunohistochemistry shown in panels B and C. B: Immunohistochemistry of the AVN showing $\alpha$-actinin in red, vimentin in blue, and Cx43 in green. C: Cx43 expression in the AVN. D-G: Higher magnification of Cx43, vimentin, and $\alpha$-actinin expression in various areas of the AVN region. H: 3D reconstruction of the AVJ split open at the plane of section shown in panels A-C. CFB: central fibrous body; IAS: interatrial septum; LNB: lower nodal bundle; VS: ventricular septum; P,A: Posterior-anterior orientation.

FIG. 18: Cx43 density in the His bundle. A: Masson trichrome stain of the His bundle. Outlined area surrounding the His bundle corresponds to immunohistochemistry shown in panels B and C. B: Immunohistochemistry of the His bundle showing $\alpha$-actinin in red, vimentin in blue, and Cx43 in green. C: Cx43 expression in the His bundle. D: Higher magnification of Cx43, vimentin, and $\alpha$-actinin expression in the His bundle. E: 3D reconstruction of the AVJ which was split open at the plane of section shown in panels A-C. CFB: central fibrous body; IAS: interatrial septum; VS: ventricular septum; P,A: Posterior-anterior orientation.

FIG. 19: Cellular Expression of Cx43. A: maximum projection image of Cx43 (green) $\alpha$-actinin (red) and vimentin (blue) staining in the lower nodal bundle (LNB). B: Colocalization of Cx43 and $\alpha$-actinin, showing that voxels of high Cx43 intensity also have a high $\alpha$-actinin signal. C: Colocalization of Cx43 and vimentin, showing that voxels of high Cx43 intensity have no significant vimentin signal. D-E: Data similar to A-C for the compact node (CN). See text for details.

FIG. 20: Cx43 density in transitional cells in the AVJ. Cx43 density in the endocardial (endo), left sided, and inferior transitional cells. All densities are normalized to the Cx43 density of the interatrial septum (IAS). DCM: dilated cardiomyopathy.

FIG. 21: Cx43 density in the conduction system of the AVJ. All densities are normalized to the Cx43 density of the interatrial septum (IAS). CN: compact AVN; DCM: dilated cardiomyopathy;

LNB: lower nodal bundle; LE: leftward extension; RE: rightward extension.

FIG. 22: 3D reconstruction of the AVJ conduction system. A-C: endocardial view of the conduction system of each normal heart. Left side of each panel displays the connective tissue and blood vessels surrounding the conduction system, as well as the location of the conduction system within the triangle of Koch of each preparation. Right side of each panel shows the conduction system and the three planes where Cx43 was quantified. D: Conduction system reconstruction of the heart with dilated cardiomyopathy. Left side of panel displays the same endocardial view as shown in A-C. Middle of panel shows the conduction system rotated 90° to more clearly show leftward extension. CFB: central fibrous body; IAS: interatrial septum; TT: tendon of Todaro; VS: ventricular septum. A-P, S-I, D-V: anterior-posterior, superior-inferior, and dorsal-ventral orientations.

| Heart | Sex | Age | Cause of Death |
|---|---|---|---|
| 1 | M | 40 | Brain Tumor |
| 2 | M | 70 | Intercerebral Hemorrhage |
| 3 | F | 58 | Intercerebral Hemorrhage |
| 4 | M | 43 | Explanted: Idiopathic Dilated Cardiomyopathy |

Patient characteristics for each sample used in this study 172×50 mm (300×300 DPI)

Cx43 Quantification

Tissue sections were taken from three different locations in the triangle of Koch: the His bundle, the compact AV nodal region, and the inferior nodal extensions. A mosaic image was created of the interatrial septum (IAS) and the tissue of the conduction system. A representative image of Cx43 staining is shown in data supplement FIG. 15A. For each region of interest, a three step algorithm determined the area of each image corresponding to Cx43 staining. First, the image was thresholded (data supplement FIG. 15B). The threshold at which the number of pixels fell below approximately 0.2% of the total number of pixels in the image was determined from the histogram of the image intensity values. This threshold was empirically determined to reproducibly select areas of Cx43 staining Once the mosaic image was thresholded, holes within areas above threshold were filled and any area above threshold consisting of less than 3.mu.m.sup.2 was discarded as noise (FIG. 15D). The amount of total tissue within each image was determined by thresholding the image at an intensity value of 10 for 8 bit images and then filling small holes (FIG. 15C). Connexin density was calculated for each image as the Cx43 area divided by the tissue area. Connexin density of the conduction system was compared to the density in the interatrial septum. All images from the same preparation were photographed using identical settings and the same thresholds were used for atrial images and conduction system images from the same preparations.

Figure and Movie Legends

Data Supplement FIG. 23: Cx43 Quantification. A: Photograph of Cx43 staining B: Image thresholded to select Cx43 staining C: The same image thresholded to select any tissue within the image. D: The thresholded image in B with the small areas above threshold removed and any black holes completely surrounded by white pixels filled. Connexin density was computed as: density=[(Cx43 area)/(tissue area)]*100.

Data Supplement Movie 1: The 3D reconstruction of a normal heart, which begins with a right endocardial view. Ventricular septum is shown in red, connective tissue in blue, atrial tissue is pink, and fat is white. As the movie plays, the tissue components surrounding the conduction system are removed to reveal the conduction system. The His bundle is shown in green, the compact AVN and leftward extension are cyan, and the lower nodal bundle and rightward extension are yellow. Veins closely associated with the conduction system are shown in purple and the AVN artery is shown in maroon.

Data Supplement Movie 2: The 3D reconstruction of the DCM heart, which begins with a right endocardial view. Ventricular septum is shown in red, connective tissue in blue, atrial tissue is pink, and fat is white. As the movie plays, the tissue components surrounding the conduction system are removed to reveal the conduction system. The His bundle is shown in green, the compact AVN and leftward extension are cyan, and the lower nodal bundle and rightward extension are yellow. Inferior transitional cells closely related to the rightward extension are orange. Veins closely associated with the conduction system are shown in purple and the AVN artery is shown in maroon. Notice that the leftward extension of this heart approaches the left side of the interatrial septum.

What is claimed is:

1. A method of providing stimulation to an inferior nodal extension of a heart, said method comprising: providing a lead comprising an electrode; positioning said electrode proximate an inferior nodal extension of a heart; and effecting at least one of activation, deactivation, or modulation of said electrode to provide stimulation to the inferior nodal extension that excites a bundle of His of the heart via an anatomical slow pathway that includes the inferior nodal extension to produce synchronized ventricular contractions.

2. The method of claim 1, wherein said electrode is provided on a tip of said lead, said step of positioning including effecting insertion of said tip into an implantation site in atrial tissue proximate the inferior nodal extension.

3. The method of claim 2, wherein said insertion site is within an anatomically effective distance from the tricuspid valve within the triangle of the Koch of the heart to provoke stimulation to the inferior nodal extension.

4. The method of claim 3, wherein said anatomically effective distance for a human is within about 5 mm to about 6 mm from the tricuspid valve within the triangle of Koch of the heart.

5. The method of claim 3, wherein said insertion comprises effecting screwing movement of said tip relative to the atrial tissue.

6. The method of claim 1, further comprising using said activation, deactivation, or modulation of said electrode to provide sympathetic stimulation to inferior nodal extension rates similar to that of the sinoatrial node of a heart.

7. The method of claim 1, further comprising using said stimulation of the inferior nodal extension for treatment of cardiac rhythm disorders of supraventricular origin.

8. The method of claim 1, further comprising using said activation, deactivation, or modulation of said electrode to accelerate an intrinsic rate of the inferior nodal extension for treatment of brady arrhythmias.

9. The method of claim 1, said activation, deactivation, or modulation of said electrode comprises delivering a sub-threshold high frequency of between about 20 Hz and about 400 Hz current to stimulate endogenous autonomic innervation surrounding the inferior nodal extension.

10. The method of claim 1, further comprising using said activating, deactivating, or modulating of said electrode to stimulate elements of the sympathetic branch of the cardiac autonomic nervous system surrounding myocytes.

11. The method of claim 1, further comprising accessing the inferior nodal extension through the superior vena cava and coronary sinus and into the atrioventricular nodal vein.

12. The method of claim 1, wherein the anatomical slow pathway bypasses a majority of an atrioventricular (AV) node, thereby minimizing an AV junction delay time.

13. A method of pacing a heart, said method comprising: providing a lead comprising an electrode; positioning said electrode within an anatomically effective distance from the tricuspid valve within the triangle of the Koch of the heart to provoke stimulation to an inferior nodal extension of the heart; and effecting at least one of activation, deactivation, or modulation of said electrode to excite a bundle of His of the heart via an anatomical slow pathway that includes the inferior nodal extension to produce synchronized ventricular contractions.

14. The method of claim 13, wherein said anatomically effective distance is within about 5 mm to about 6 mm of the tricuspid valve within the triangle of Koch of the heart.

15. The method of claim 13, wherein the anatomical slow pathway bypasses a majority of an atrioventricular (AV) node, thereby minimizing an AV junction delay time.

16. A method of providing stimulation to an inferior nodal extension of a heart, said method comprising: providing a lead comprising an electrode; and providing instructions to: effect movement of said lead such that said electrode is positioned proximate an inferior nodal extension of a heart; and effect at least one of activation, deactivation, or modulation of said electrode to provide stimulation to the inferior nodal extension that excites a bundle of His of the heart via an anatomical slow pathway that includes the inferior nodal extension to produce synchronized ventricular contractions.

17. The method of claim 16, further comprising providing instructions to access the inferior nodal extension through the superior vena cava and coronary sinus and into the atrioventricular nodal vein.

18. The method of claim 16, wherein said electrode is provided on a tip of said lead, said step of positioning comprising effecting insertion of said tip into a site in atrial tissue proximate the inferior nodal extension.

19. The method of claim 18, wherein said insertion site is within about 5 mm to about 6 mm of the tricuspid valve within the triangle of Koch of the heart.

20. The method of claim 16, wherein the anatomical slow pathway bypasses a majority of an atrioventricular (AV) node, thereby minimizing an AV junction delay time.

* * * * *